(12) United States Patent
Missfeldt

(10) Patent No.: US 6,649,335 B2
(45) Date of Patent: Nov. 18, 2003

(54) CYANINE DYE

(75) Inventor: Michael Missfeldt, Leichlingen (DE)

(73) Assignee: AGFA-Gevaert (BE)

( * ) Notice: Subject to any disclaimer, the term of this patent is extended or adjusted under 35 U.S.C. 154(b) by 94 days.

(21) Appl. No.: 10/011,560

(22) Filed: Nov. 5, 2001

(65) Prior Publication Data

US 2002/0127502 A1 Sep. 12, 2002

(30) Foreign Application Priority Data

Nov. 7, 2000 (DE) .......................... 100 55 093

(51) Int. Cl.$^7$ .................. G03C 1/005; G03C 1/494
(52) U.S. Cl. .................. 430/576; 430/570; 430/577; 430/581; 430/583; 430/585; 430/567
(58) Field of Search ................ 430/570, 576, 430/577, 581, 583, 585, 567

(56) References Cited

U.S. PATENT DOCUMENTS

| | | | | |
|---|---|---|---|---|
| 3,985,763 | A | 10/1976 | Harnisch | 260/307 |
| 4,184,876 | A | 1/1980 | Eeles et al. | 430/505 |
| 5,415,980 | A | 5/1995 | Ohshima | 430/376 |
| 5,512,428 | A | 4/1996 | Missfeldt | 430/583 |
| 5,674,674 | A | 10/1997 | Edwards et al. | 430/567 |
| 6,333,146 | B1 * | 12/2001 | Kobayashi et al. | 430/570 |

FOREIGN PATENT DOCUMENTS

| | | |
|---|---|---|
| DE | 3541098 | 5/1987 |
| EP | 222970 | 5/1987 |
| EP | 565121 | 10/1993 |
| EP | 608 955 | 8/1994 |
| EP | 990 650 | 4/2000 |
| FR | 2338041 | 8/1977 |

OTHER PUBLICATIONS

Menichi, G. et al., "Examinations Related to Benzofurane," *Bull. Soc. Chim. France* 7: p. 2352–2354 (1973) With translation of the title and the summary.
Abramenko, P.I. et al. "Polymethine Dyes, Derivatives of Thieno– and Benzothienobenzoxazoles and Benzofurobenzoxazoles" *Chemical Abstr.* 89:164917t (1978) (Sb. Nauch. Tr. Vses. –i. I Proekt. In–t Khim. –fotogr. Prom–sti 25 (1977) p. 25–37.

* cited by examiner

Primary Examiner—Geraldine Letscher
(74) Attorney, Agent, or Firm—Connolly Bove Lodge & Hutz LLP

(57) ABSTRACT

A cyanine dye of formula (II)

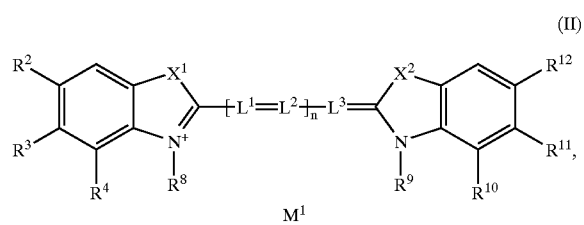

wherein $X^1$ is $C(R^5, R^6)$, $NR^7$, O, S or Se, $X^2$ is O, S, Se or $NR^{13}$, $R^2$ with $R^3$, or $R^3$ with $R^4$, are the remaining members for the completion of a condensed furano ring system, and the other $R^2$ or $R^4$ radical, is H, a halogen, SH, CN, $CF_3$, alkyl, aryl, heterocyclyl, alkoxy, aryloxy, alkylthio or arylthio, $R^{10}$ to $R^{12}$, are H, a halogen, SH, CN, $CF_3$, alkyl, aryl, heterocyclyl, alkoxy, aryloxy, alkylthio or arylthio, or $R^{10}$ with $R^{11}$, or $R^{11}$ with $R^{12}$, are the remaining members for the completion of a ring system, $R^5$ to $R^7$ and $R^{13}$ are alkyl, alkylene-$SO_3Z^1$ or alkylene-$CO_2Z^1$, $R^8$ and $R^9$ are alkyl, alkylene-$SO_3Z^1$, alkylene-$CO_2Z^1$ or alkylene-$Y^2$—$N(Z^1)$—$Y^3$-alkyl, $Z^1$ is H or a negative charge, $Y^2$ and $Y^3$ are —S(=O)$_2$— or —C(=O)—, $M^1$ is a counterion, $L^1$, $L^2$ and $L^3$ are a methine group and n is 0, 1, 2 or 3.

15 Claims, No Drawings

CYANINE DYE

This invention relates to new heterocyclic compounds, particularly spectral sensitisers of the cyanine dye type, and to intermediates for the synthesis thereof. The invention also relates to photographic silver halide materials which contain these new compounds.

It is known that cyanine dyes can be used for the spectral sensitisation of silver halide emulsions. Various measures have been disclosed in order to achieve a further increase in speed, such as special substituted cyanine dyes in U.S. Pat. No. 5,674,674 and a combination of two trimethine cyanines in EP 608 955, for example. In order to reduce fogging, anti-fogging agents are known, for example, which often comprise mercapto-substituted heterocycles. Cyanine dyes which result in a low degree of fogging are described in U.S. Pat. No. 5,415,980.

With these known spectral sensitisers, however, no success has been achieved in producing photographic materials of very high speed which are simultaneously distinguished by a low degree of fogging. Using these known measures, an increase in speed is usually accompanied by an increase in fogging, and measures for reducing fogging generally result in a loss of speed. Moreover, at the large amounts which are necessary for high speeds, the known sensitisers often result in unwanted staining of the processed materials due to spectral sensitisers which have not been removed by washing (sensitiser staining). However, in order to fulfil the ever-increasing demands as regards image quality which are imposed even on high-speed photographic materials a very high speed/fogging ratio and a low degree of sensitiser staining are indispensable.

The underlying object of the present invention is thus to provide new spectral sensitisers, the use of which results in photographic materials which are distinguished by very high speed, low fogging and a low degree of sensitiser staining.

Surprisingly, it has now been found that is achieved if new spectral sensitisers are used, of the type comprising cyanine or merocyanine dyes, which at one end of their methine chain comprise a heterocycle derived from indole with a condensed-on furan ring.

The present invention therefore relates to a heterocyclic compound corresponding to formula (I)

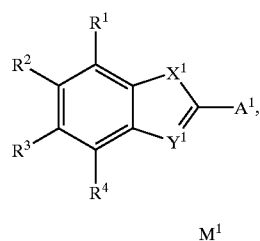

(I)

wherein $X^1$ denotes $C(R^5, R^6)$, $NR^7$, O, S or Se, $Y^1$ denotes N or $N^{(+)}$—$R^8$, $A^1$ denotes H or an organic radical, at least one of the combinations $R^1$ with $R^2$, $R^2$ with $R^3$ or $R^3$ with $R^4$ denote the remaining members for the completion of a substituted or unsubstituted condensed furanoring system, and the $R^1$ to $R^4$ radicals, which are not part of the furan ring system, independently of each other denote H, a halogen, SH, CN, $CF_3$, alkyl, phenyl, aryl, heterocyclyl, alkoxy, aryloxy, alkylthio or arylthio, $R^5$ to $R^7$ denote alkyl, alkylene-$SO_3Z^1$ or alkylene-$CO_2Z^1$, wherein the alkyl and alkylene can be can be further substituted and each comprise 1 to 6 C atoms, particularly 1 to 4 C atoms, $R^8$ denotes alkyl, alkylene-$SO_3Z^1$, alkylene-$CO_2Z^1$ or alkylene-$Y^2$—$N(Z^1)$—$Y^3$-alkyl, wherein alkyl and alkylene can be further substituted and each comprise 1 to 6 C atoms, $Z^1$ denotes H or a negative charge, $Y^2$, $Y^3$, independently of each other, denote —$S(=O)_2$— or —$C(=O)$—, and $M^1$ denotes a counterion which may be necessary for charge equalisation, wherein $R^1$ with $R^2$ or $R^3$ with $R^4$, provided that they are not part of the furan ring system, can also each jointly denote the remaining members for the completion of a substituted or unsubstituted condensed-on benzene or naphthalene ring system, and wherein $Y^1$ has the meaning $N^{(+)}$—$R^8$ if $A^1$ denotes the remaining members of a cyanine dye.

The oxygen of the furan ring can assume any of the three free positions, but is preferably bonded directly to the benzene nucleus of formula (I).

The two hydrogen atoms of the furan ring system can, independently of each other, be substituted by a halogen, CN, $CF_3$, an alkyl, phenyl, aryl, heterocyclyl, alkoxy, aryloxy, alkylthio or arylthio or can jointly be substituted by the remaining members for the completion of a substituted or unsubstituted condensed-on benzene or naphthalene ring system. The furan ring system is preferably unsubstituted.

The alkyl, alkenyl and alkylene groups in the sense of the present invention can be straight chain, branched or cyclic.

The alkyl, alkenyl, alkylene, aryl and heterocyclyl groups can be substituted, for example, by alkyl, alkenyl, alkyne, alkylene, aryl, heterocyclyl, hydroxy, carboxy, halogen, alkoxy, aryloxy, heterocyclyloxy, alkylthio, arylthio, heterocyclylthio, alkylseleno, arylseleno, heterocyclylseleno, acyl, acyloxy, acylamino, cyano, nitro, amino, thio or mercapto groups, wherein a heterocyclyl represents a saturated, unsaturated or aromatic heterocyclic radical and an acyl represents the radical of an aliphatic, olefinic or aromatic carboxylic, carbamic, carbonic, sulphonic, amidosulphonic, phosphoric, phosphonic, phosphorous, phosphinic or sulphinic acid.

Compounds of formula (I) are preferred in which $A^1$ denotes H, alkyl, alkenyl or the remaining members of a cyanine or mero-cyanine dye, and only one of the combinations $R^1$ with $R^2$, $R^2$ with $R^3$ or $R^3$ with $R^4$ denotes the remaining members for the completion of a substituted or unsubstituted condensed-on furan ring system.

In one preferred embodiment of the invention, the new compounds are cyanine dyes of formula (II)

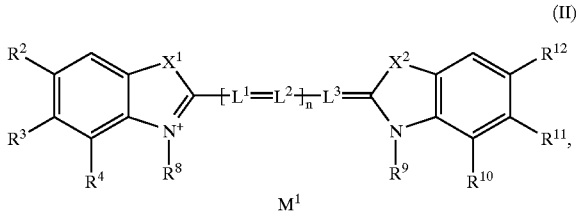

(II)

wherein $X^2$ denotes O, S, Se or $NR^{13}$, $R^2$ with $R^3$, or $R^3$ with $R^4$, each jointly denote the remaining members for the completion of a substituted or unsubstituted condensed furanoring system, and the $R^2$ or $R^4$ radical, which is not part of the furan ring system, denotes H, a halogen, SH, CN, $CF_3$, alkyl, phenyl, aryl, heterocyclyl, alkoxy, aryloxy, alkylthio or arylthio, $R^{10}$ to $R^{12}$, independently of each other, denote H, a halogen, SH, CN, $CF_3$, alkyl, phenyl, aryl, heterocyclyl, alkoxy, aryloxy, alkylthio or arylthio, or $R^{10}$ with $R^{11}$, or $R^{11}$ with $R^{12}$, each jointly denote the remaining members for the completion of a substituted or unsubstituted condensed furano, benzene or naphthalene ring system, and the $R^{10}$ or $R^{12}$ radical, which is not part of the ring system, denotes H, a halogen, SH, CN, $CF_3$, alkyl, phenyl, aryl, heterocyclyl, alkoxy, aryloxy, alkylthio or arylthio, $R^9$ denotes alkyl, alkylene-$SO_3Z^1$, alkylene-$CO_2Z^1$ or alkylene-$Y^2$—$N(Z^1)$—$Y^3$-alkyl, wherein the alkyl and alkylene can be further substituted and each comprise 1 to 6 C atoms, $R^{13}$ denotes alkyl, alkylene-$SO_3Z^1$ or alkylene-$CO_2Z^1$, wherein the alkyl and alkylene can be further substituted and each comprise 1 to 6 C atoms, $L^1$, $L^2$, $L^3$ denote a substituted or unsubstituted methine group, which can be a constituent of one or more carbocyclic rings, n denotes 0, 1, 2 or 3, particularly 0, 1 or 2, and wherein the other substituents have the meanings given above.

Of the possible variants, sensitisers comprising an arrangement of the furan ring system corresponding to formulae (III) or (IV) are particularly advantageous

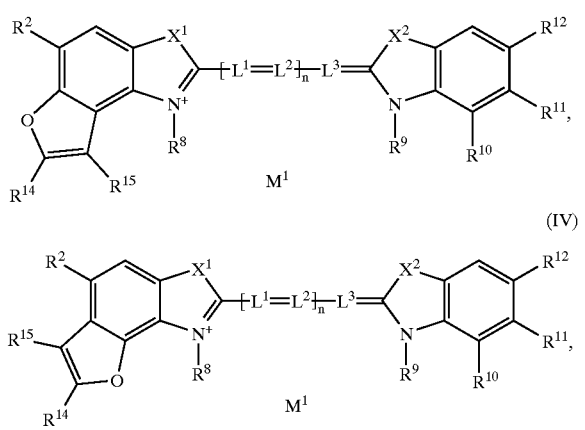

wherein $R^{14}$, $R^{15}$ independently of each other, denote H, a halogen, CN, $CF_3$, alkyl, phenyl, aryl, heterocyclyl, alkoxy, aryloxy, alkylthio or arylthio, and wherein the other substituents have the meanings given above. It is preferable if $R^{14}$ and/or $R^{15}$, particularly $R^{14}$ and $R^{15}$, denote H.

Particularly high speeds can be obtained using a cyanine dye according to formula (II), and particularly according to formulae (III) and (IV), in which $X^1$ denotes S or Se, and $R^{10}$ to $R^{12}$ independently of each other, denote H, a halogen, CN, $CF_3$, alkyl, phenyl, aryl, heterocyclyl, alkoxy, aryloxy, alkylthio or arylthio, wherein $R^{10}$ with $R^{11}$ or $R^{11}$ with $R^{12}$ can each jointly denote the remaining members for the completion of a substituted or unsubstituted condensed benzene or naphthalene ring system.

The new compounds of formula (V)

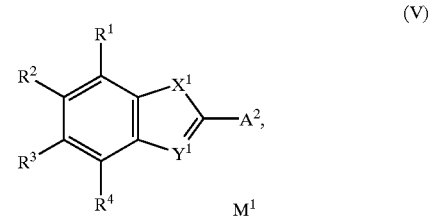

wherein $A^2$ denotes H, alkenyl or alkyl, and wherein the other substituents have the meanings given above, can be used for the production of the spectral sensitisers described above. The compounds (V) which are preferred for this purpose are those in which $R^1$ denotes hydrogen, $A^2$ denotes methyl, and $X^1$ denotes S or Se.

In one particularly preferred embodiment of the invention, a heterocyclyl represents an aromatic radical, particularly 2-thienyl, 3-thienyl, 1-pyrrolyl, 2-pyrrolyl, 2-furanyl, 3-furanyl, benzthienyl or indolyl.

The new compounds of formula (I) are advantageously used in photographic materials, wherein the preferred photographic materials are those which comprise a support and at least one light-sensitive silver halide emulsion layer and which, in their silver halide emulsion layer, contain at least one compound of formula (I), particularly at least one spectral sensitiser of formula (II), most preferably at least one sensitiser of formulae (III) or (IV).

The speed of the silver halide emulsion layer which is sensitised according to the invention can be increased in the known manner by the admixture of a plurality of sensitisers.

In one preferred embodiment, the photographic material contains at least two, particularly at least three different sensitiser structures in the at least one silver halide emulsion layer, at least one of which sensitiser structures corresponds to formulae (II), (III) or (IV).

In one particularly preferred embodiment, the photographic material contains at least two different sensitisers of formulae (II), (III) or (IV) in the same silver halide emulsion layer.

Surprisingly, a particularly favourable speed/fogging ratio is achieved if, in addition to at least one sensitiser of formulae (II), (III) or (IV), the photographic material contains at least one dye of formula (VI) in the same silver halide emulsion layer.

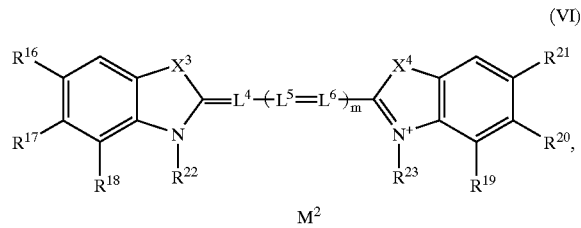

wherein $X^3$, $X^4$, independently of each other, denote O, S, Se or $NR^{24}$, $R^{16}$ to $R^{21}$, independently of each other, denote H, a halogen, CN, $CF_3$, alkyl phenyl, aryl, heterocyclyl, alkoxy, aryloxy, alkylthio or arylthio, $R^{22}$, $R^{23}$, independently of each other, denote alkyl, alkylene-$SO_3Z^2$, alkylene-$CO_2Z^2$ or alkylene-$Y^4$—N($Z^2$)—$Y^5$-alkyl, wherein the alkyl and alkylene can be further substituted and each comprise 1 to 6 C atoms, $R^{24}$ denotes alkyl, alkylene-$SO_3Z^2$ or alkylene-$CO_2Z^2$, wherein the alkyl and alkylene can be further substituted and each comprise 1 to 6 C atoms, particularly 1 to 4 C atoms, $Z^2$ denotes H or a negative charge, $L^4$, $L^5$, $L^6$ denote a substituted or unsubstituted methine group, which can be a constituent of one or more carbocyclic rings, m denotes 0 or 1, $Y^4$, $Y^5$, independently of each other, denote —S(=O)$_2$— or —C(=O)—, and $M^2$ denotes a counterion which may be necessary for charge equalisation, wherein either $R^{16}$ with $R^{17}$ or $R^{17}$ with $R^{18}$ and/or either $R^{19}$ with $R^{20}$ or $R^{20}$ with $R^{21}$ can each jointly denote the remaining members for the completion of a substituted or unsubstituted condensed benzene or naphthalene ring system.

Particularly pronounced advantages, especially as regards fogging, have been identified for photographic materials according to the invention which in at least one silver halide emulsion layer contain silver halide crystals, at least 95 mol percent of which consist of silver chloride, and which contain not more than 1 mol percent of silver iodide.

In a further advantageous embodiment, the photographic material contains at least one sensitiser of formulae (II), (III) or (IV), wherein n is equal to 0, in at least one silver halide emulsion layer which contains at least one yellow coupler.

The advantages of the sensitisers according to the invention are particularly pronounced for the sensitisation of tabular crystals with an aspect ratio of at least 3:1, particularly if the aspect ratio thereof is greater than 6:1, and even more advantageously if said aspect ratio is greater than 10:1.

The compounds according to the invention can also be used advantageously for the sensitisation of emulsions which mainly contain silver bromide and which have a bromide content of at least 80 mol %, a maximum chloride content of 15 mol % and a maximum iodide content of 12 mol %.

The compounds of formula (I) can be contained in one or more layers of the material and can be added by customary methods, e.g. as a solution or a dispersion. The addition can be made, for example, to at least one casting solution before casting the material, or can be made at any time during the production of at least one silver halide emulsion of the material.

Compounds (I), (II), (III) or (IV) are preferably added after precipitation of the silver halide emulsion, wherein further advantages can be obtained if the chemical ripening thereof with gold and chalcogen compounds is conducted, at least in part, in the presence of at least one of compounds (I), (II), (III) or (IV), and if sulphur and/or selenium and/or tellurium compounds which are labile with respect to silver halides are used as chalcogen compounds.

Compounds of formula (I), and particularly compounds of formulae (II), (III) and (IV), are preferably contained in the material, in each layer in which they are used, in an amount of $5·10^{-6}$ to $5·10^{-3}$ mol/mol silver halide, particularly in an amount of $1·10^{-4}$ to $2·10^{-3}$ mol/mol silver halide.

Other preferred embodiments of the invention are given in the subsidiary claims. Particularly suitable sensitisers of formula (II) are given below.

II-6 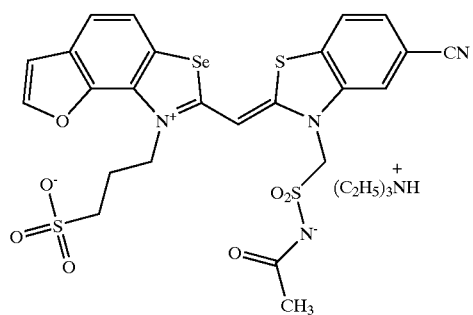
II-7 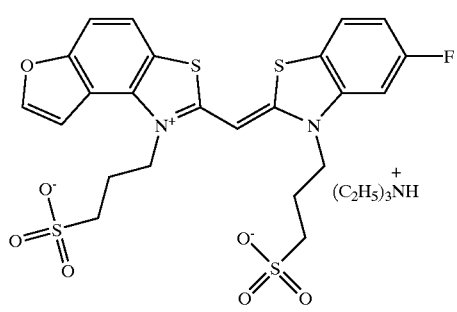
II-8 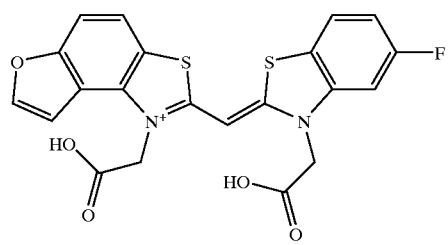
II-9 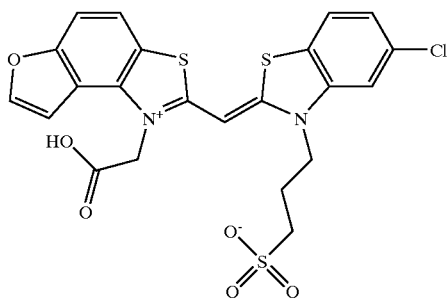
II-10 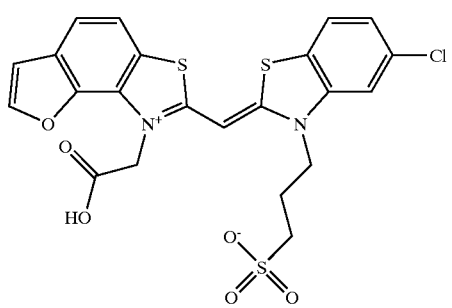
II-11 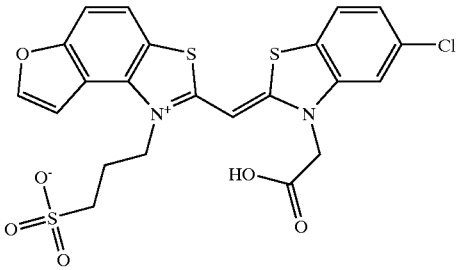
II-12 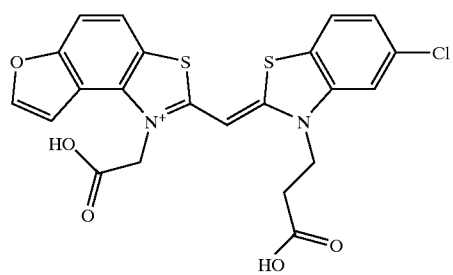
II-13 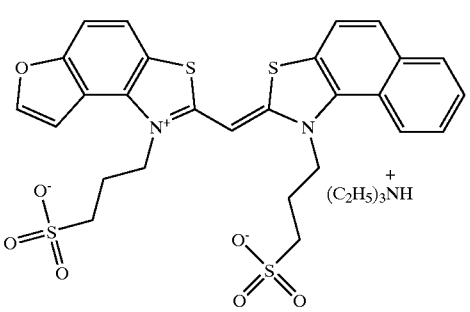
II-14 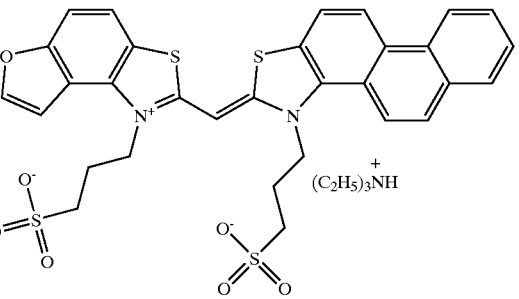
II-15 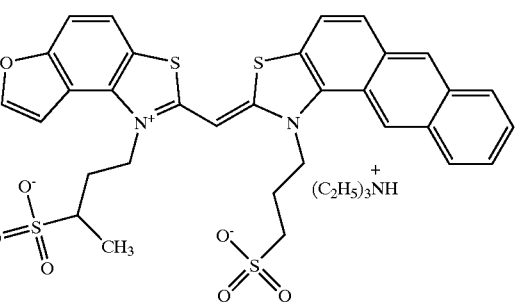

II-16
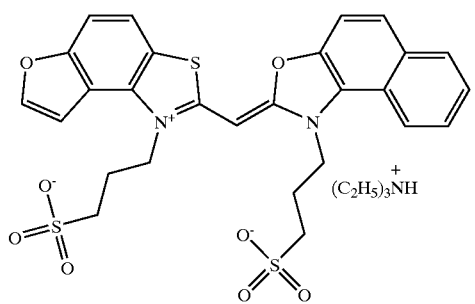
II-21
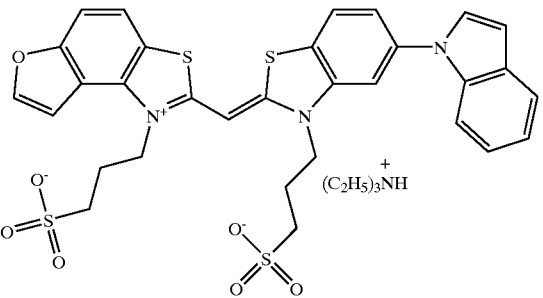
II-17
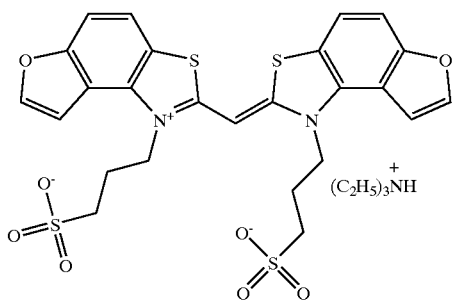
II-22
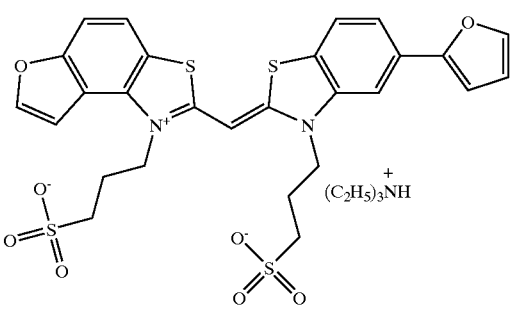
II-18
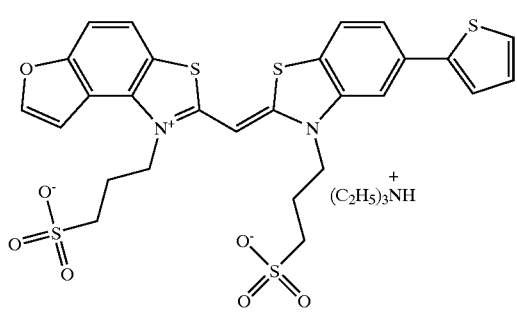
II-23
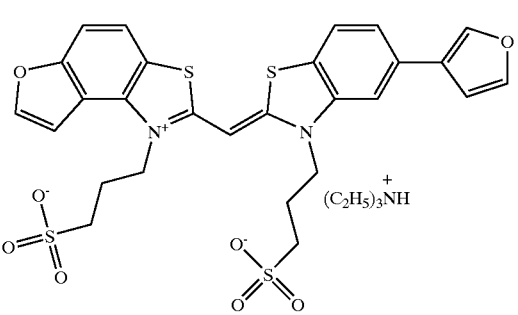
II-19
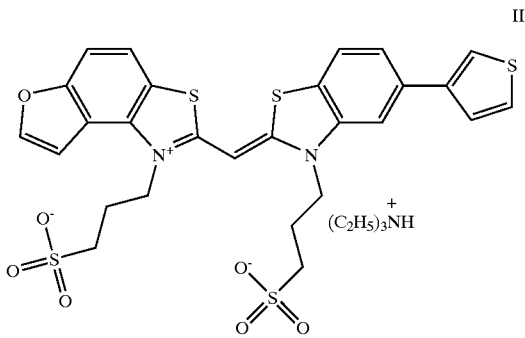
II-24
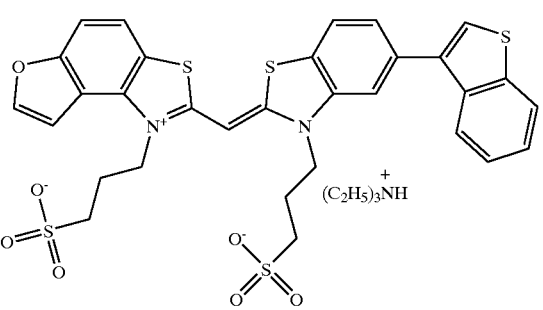
II-20
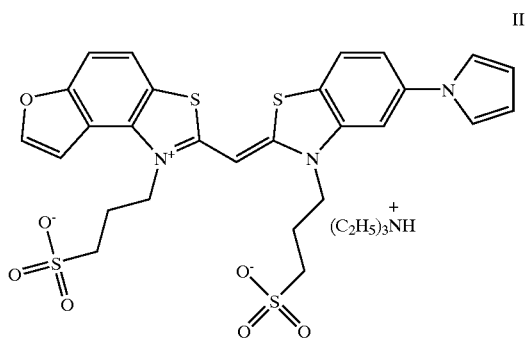
II-25
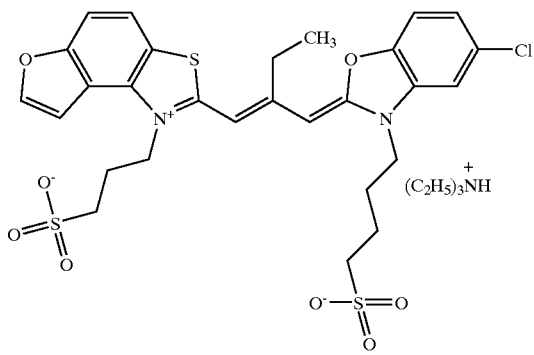

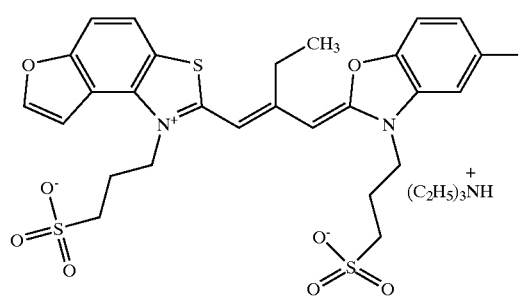
II-26
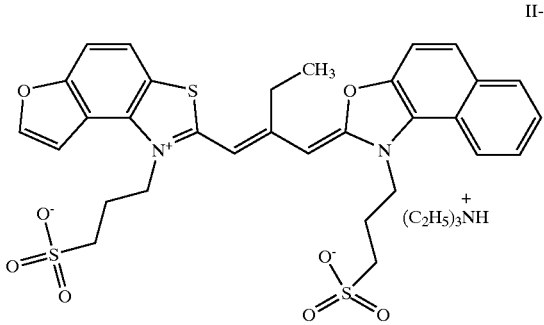
II-27
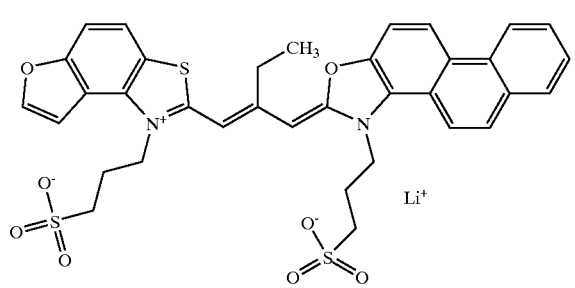
II-28
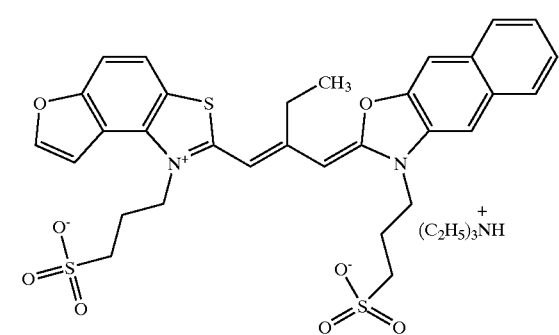
II-29
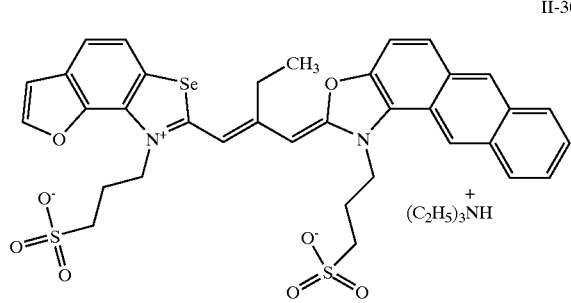
II-30
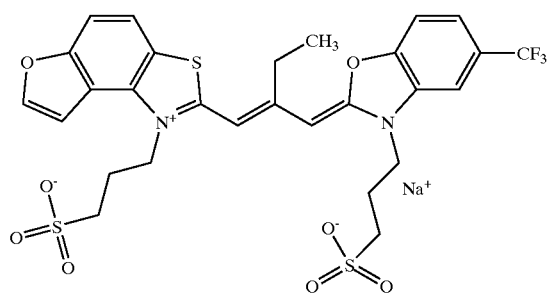
II-31
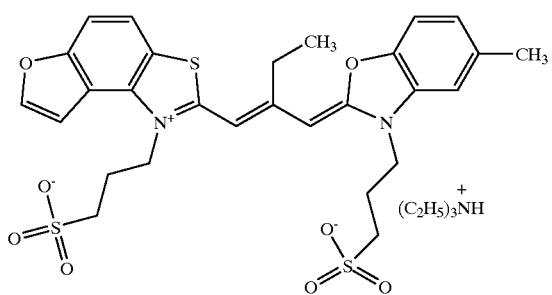
II-32
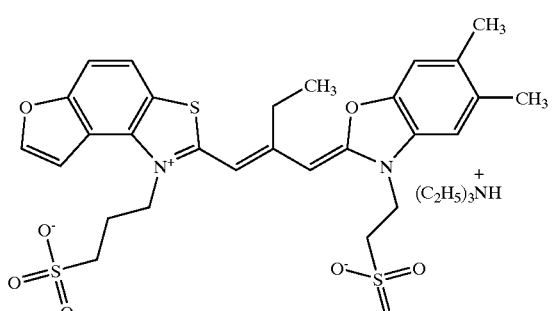
II-33
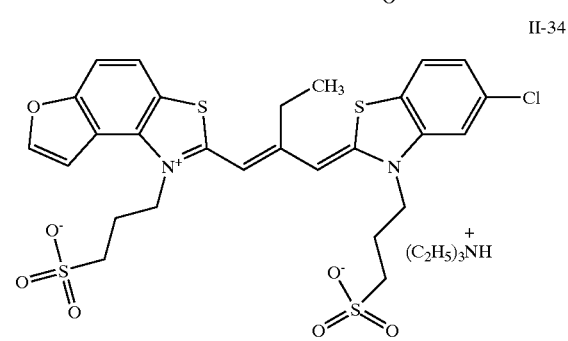
II-34
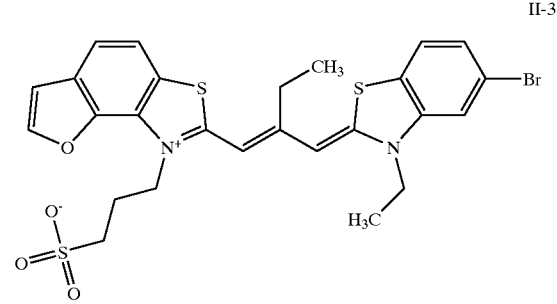
II-35

II-36
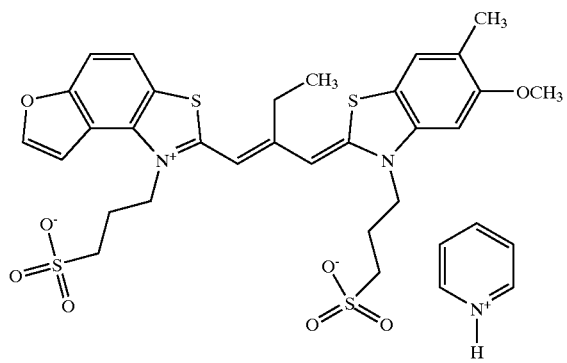
II-37
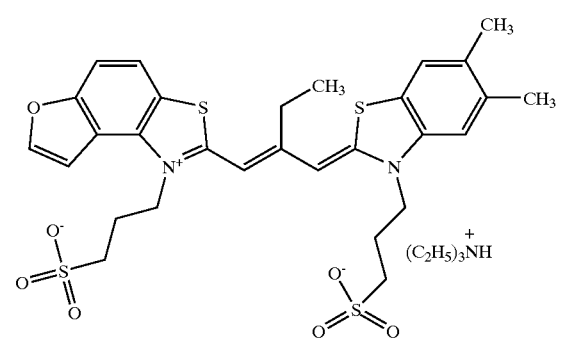
II-38
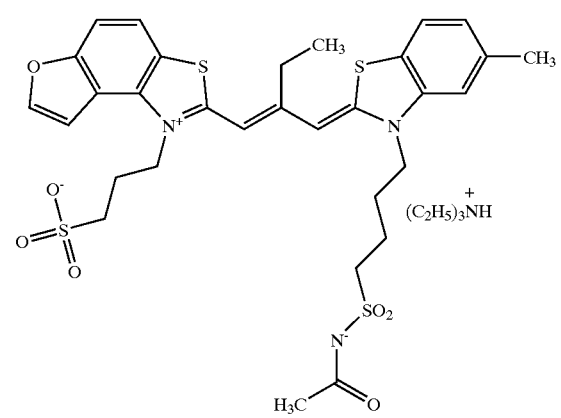
II-39
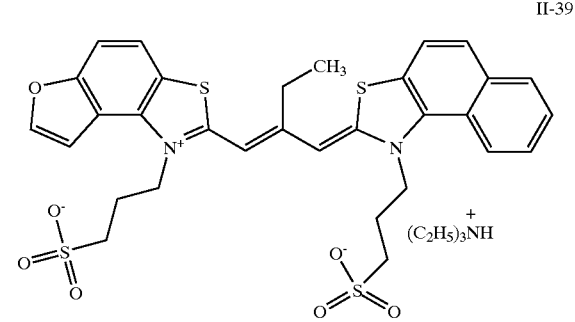
II-40
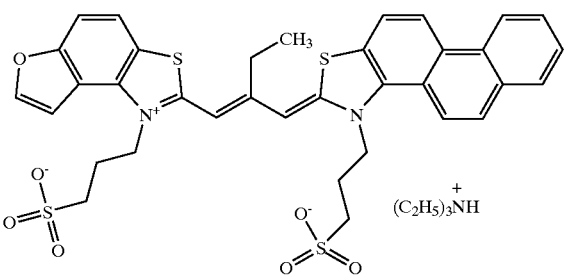
II-41
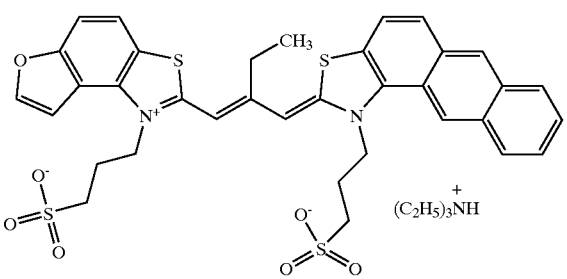
II-42
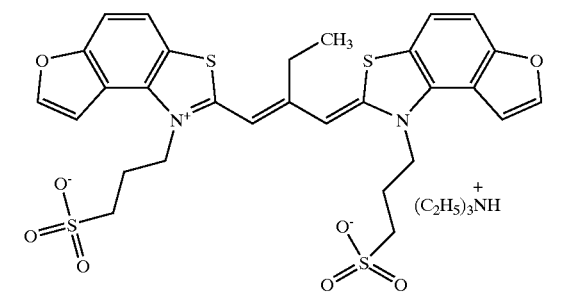
II-43
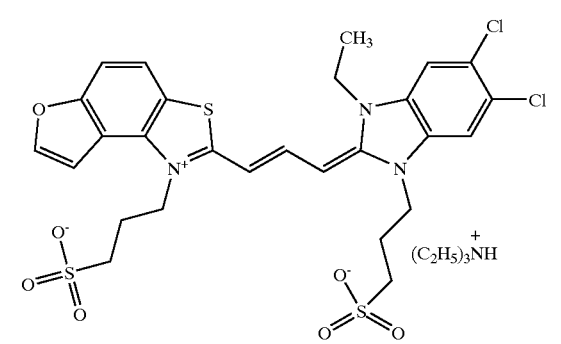
II-44
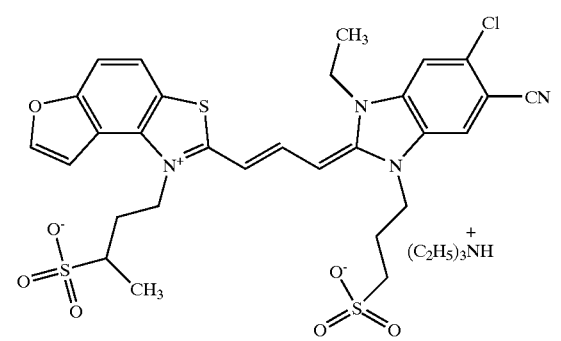

II-45
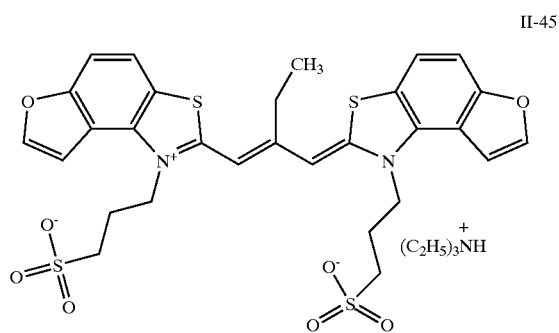
II-46
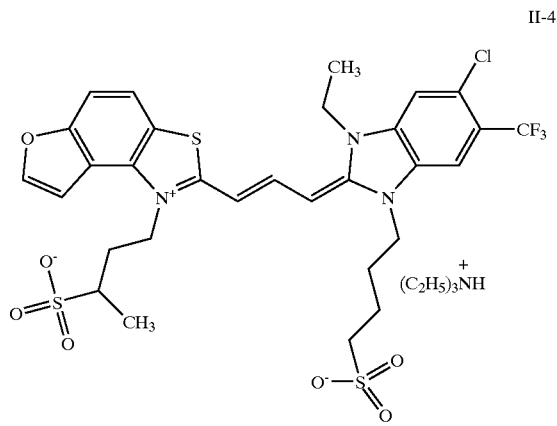
II-47
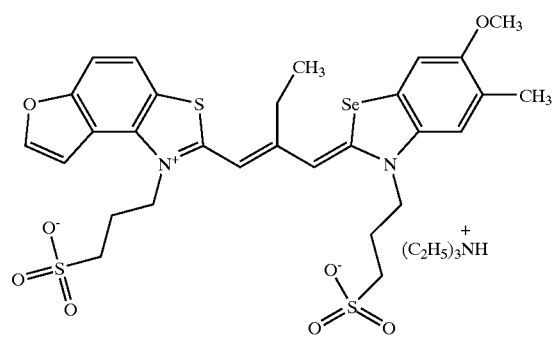
II-48
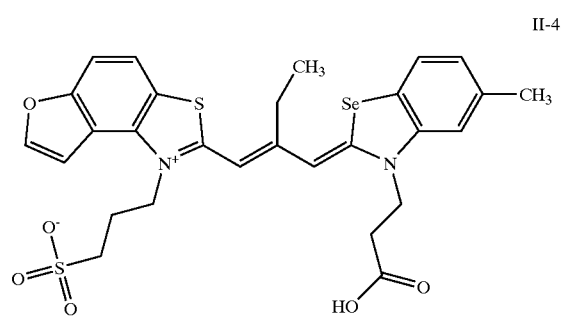
II-49
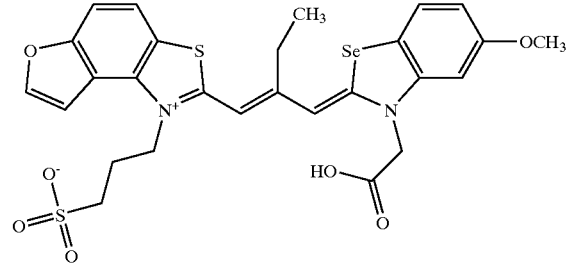
II-50
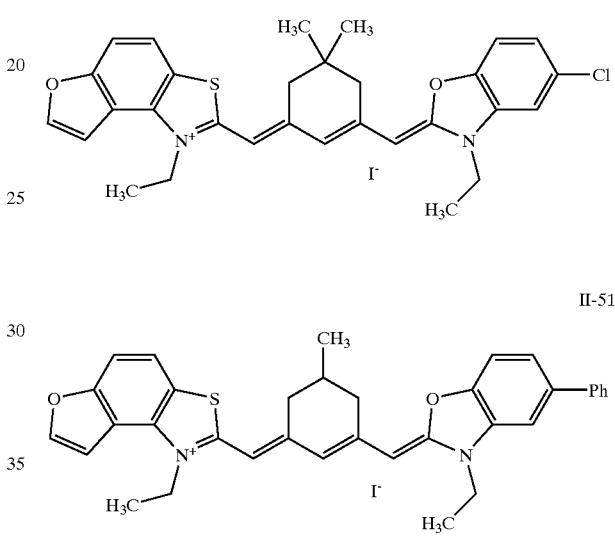
II-51
II-52
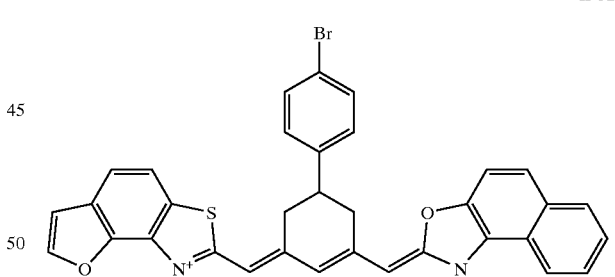
II-53
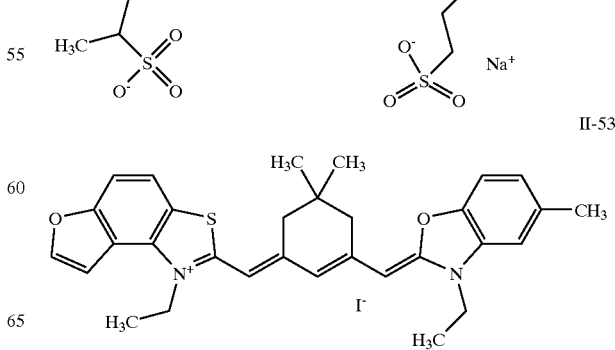

II-54
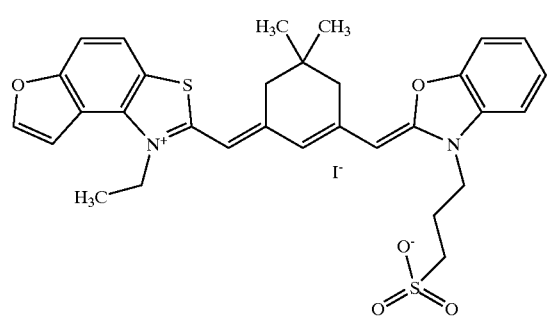
II-55
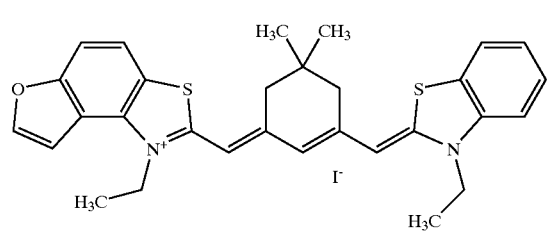
II-56
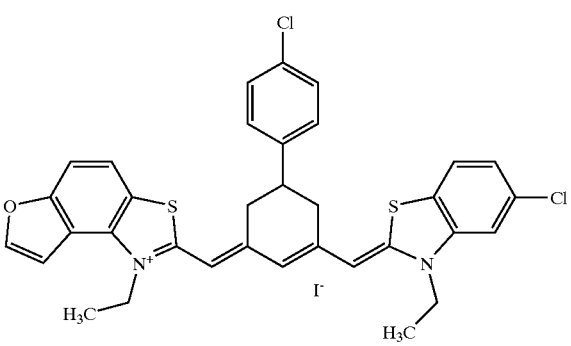
II-57
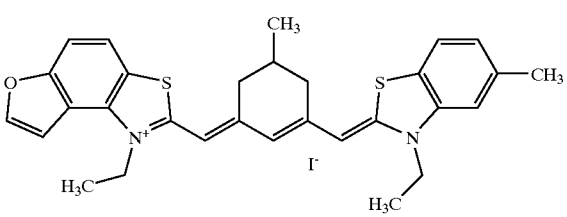
II-58
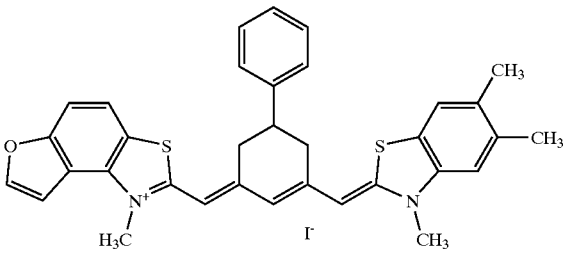
II-59
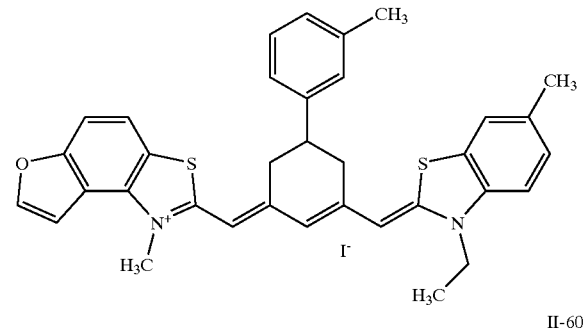
II-60
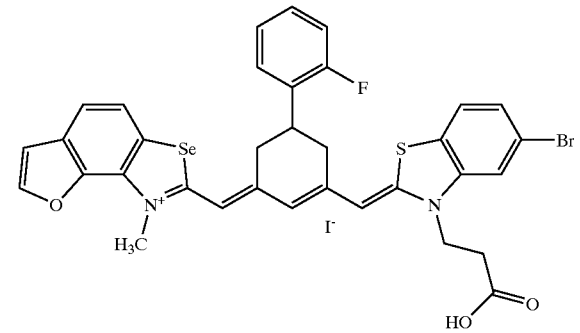
II-61
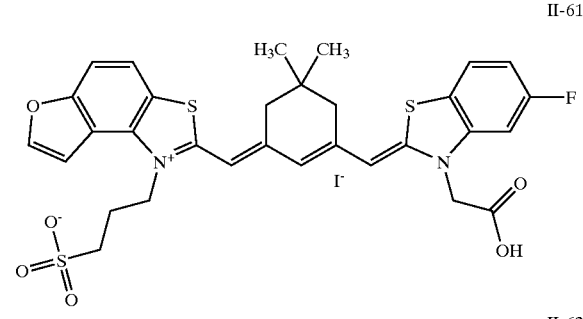
II-62
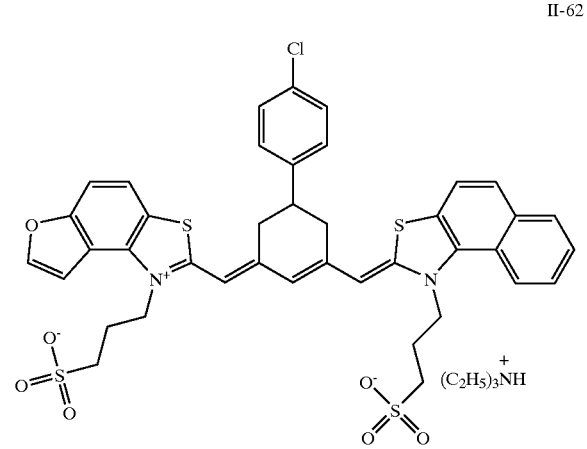
II-63
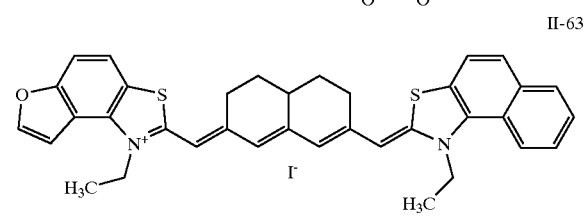

II-64
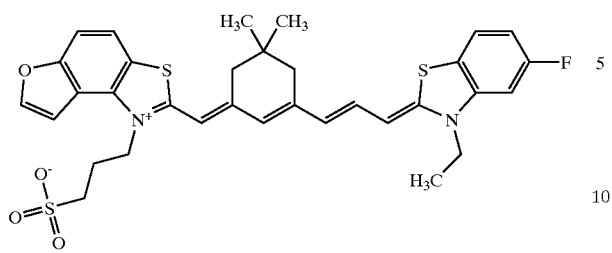
Particularly suitable sensitizers of formula (VI) are given below:
VI-1
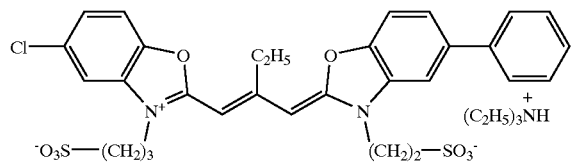
VI-2
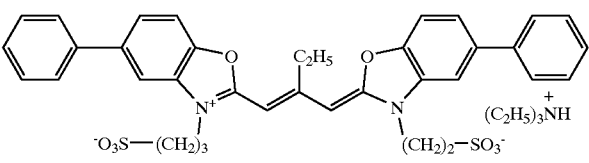
VI-3
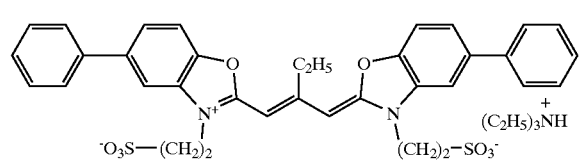
VI-4
VI-5
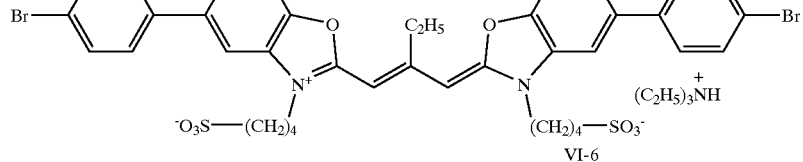
VI-6
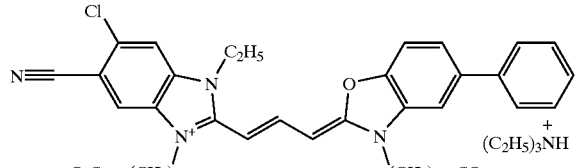
VI-7
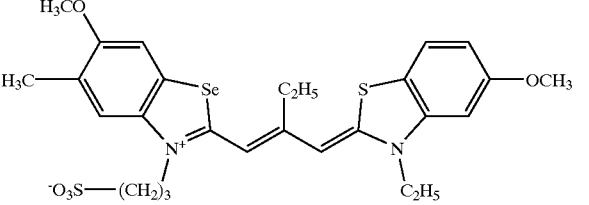
VI-8
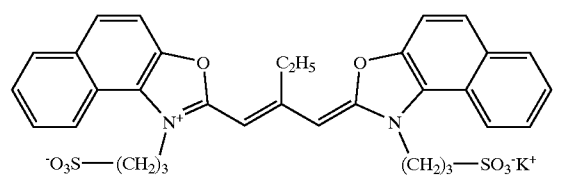
VI-9
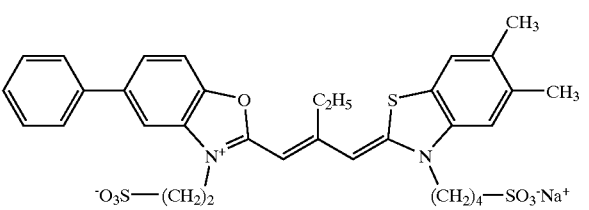
VI-10
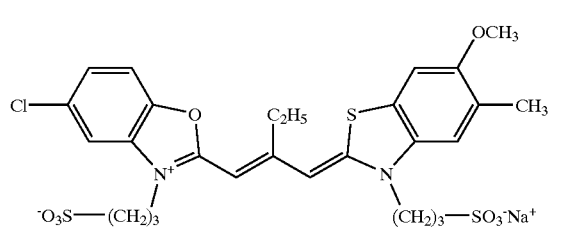
VI-11
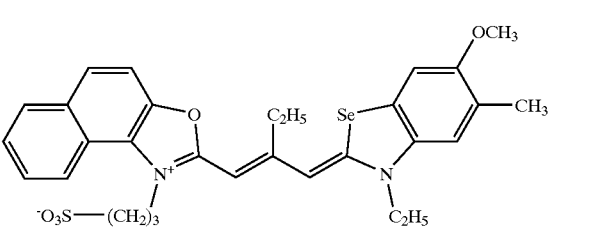

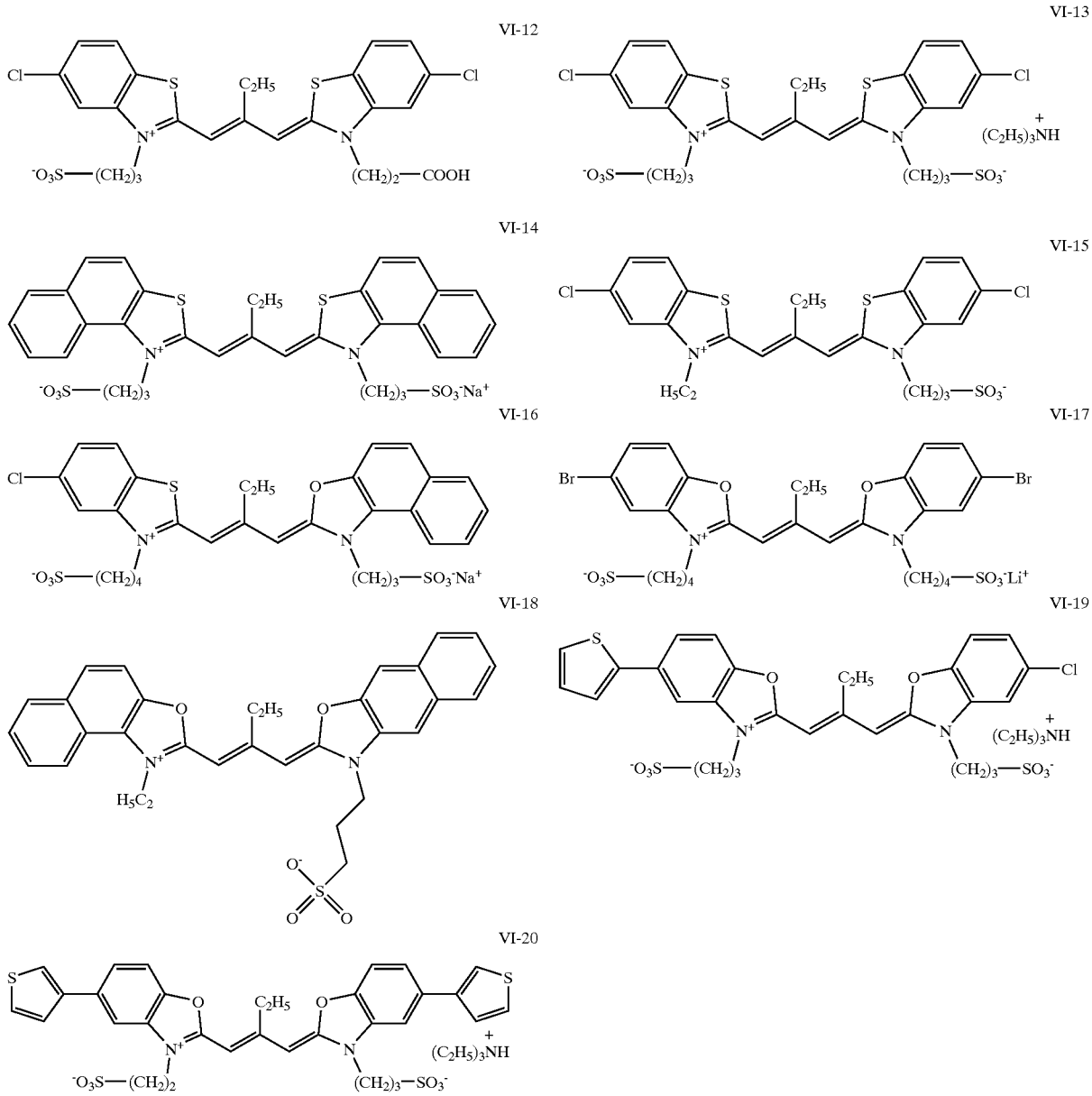

The following Examples illustrate possible methods of synthesis for preparing substances of formula (I) according to the invention; these methods can easily be varied by one skilled in organic synthesis. Moreover, the compounds of formula (I) are not limited to those which can be obtained by the methods of synthesis exemplified here.

Sensitiser II-1 can be obtained by the following synthesis route:

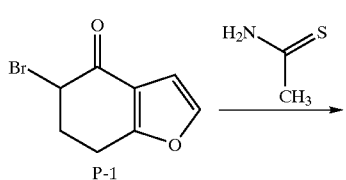

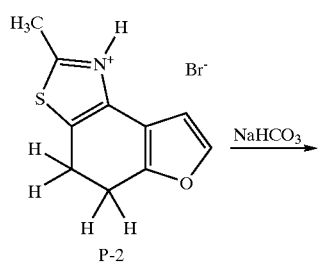

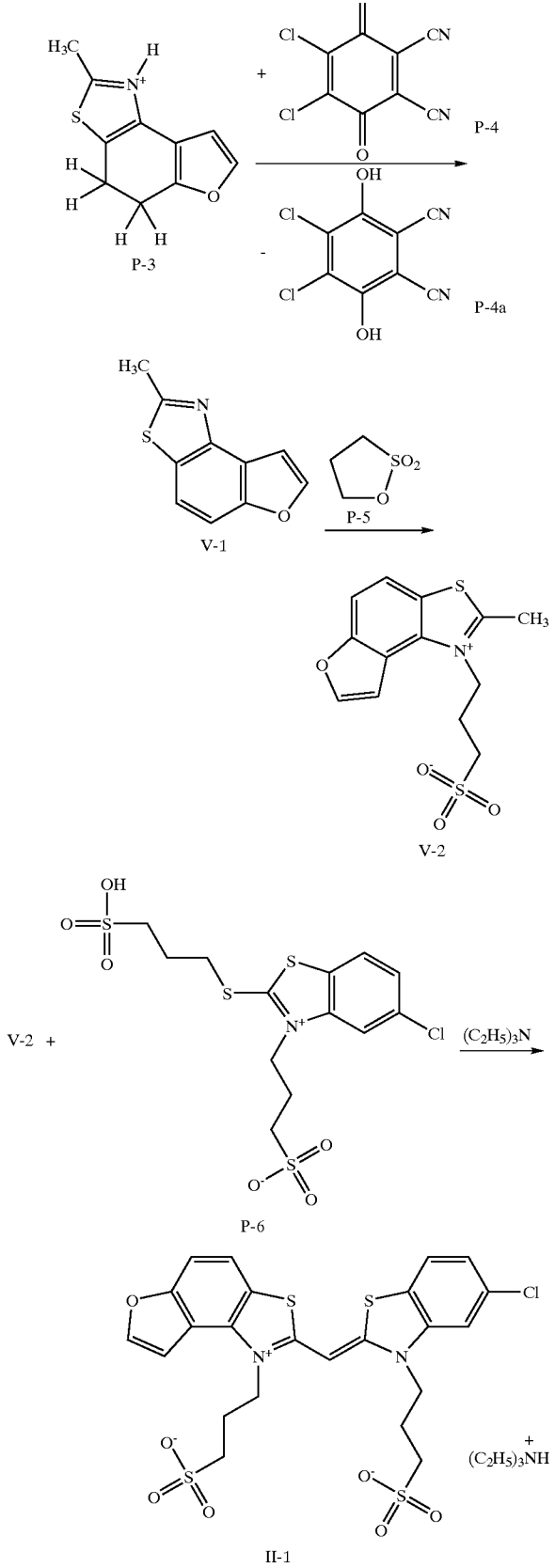

Synthesis of P-3

50.3 g (208 mmol) P-1, obtained as described by W. A. Remers and G. S. Jones, J. Heterocyclic Chem. (12), 421 (1975), and 18.7 g (249 mmol) thioacetamide were heated at 85–87° C. in 170 ml dimethylformamide (DMF) with stirring for 2.5 hours. After cooling to 5° C., the precipitated hydrobromide P-2 was filtered off under suction and thoroughly washed with DMF. P-2 was dissolved in 400 ml water, and thereafter the solution was adjusted to pH=8 by adding aqueous $NaHCO_3$ solution and was stirred for 30 minutes. The precipitated thiazole base P-3 was filtered off under suction, thoroughly washed with water, and dried under vacuum at 40° C. Yield: 25.6 g P-3 (82.7% theoretical).

Synthesis of V-1

23 g (120 mmol) P-3 were dissolved in 1 l $CHCl_3$. 32.7 g (144 mmol) 2,3-dichloro-5,6-dicyano-benzoquinone, P-4, were added in portions thereto with stirring at 18–22° C. over 1.5 hours, and thereafter the batch was stirred for a further 1.5 hours at the given temperature. After adding a further liter of $CHCl_3$, 300 g bleaching earth were added and the batch was stirred for 30 minutes at room temperature. The bleaching earth was filtered off under suction and the residue was washed with $CHCl_3$. This procedure was repeated until hydroquinone P-4a could no longer be detected (thin layer chromatography tests; as a rule the treatment with bleaching earth had to be performed 3 times in total). After removing the chloroform under vacuum and drying the residue under vacuum at 40° C., 15.6 g V-1 were obtained (68.7% theoretical).

Synthesis of V-2

3.78 g (0.02 mol) V-1 and 2.44 g (0.02 mol) 1,3-propanesulphone P-5 were dissolved in 10 ml 1,2-dichlorobenzene and the batch was heated for 6 hours at 122–125° C. with stirring. After cooling to room temperature, the precipitated quaternary salt was filtered off under suction and washed thoroughly with 1,2-dichlorobenzene, and the residue was extracted by boiling it for 1 hour with 60 ml acetone. Yield: 5.1 g V-2 (81.9% theoretical).

Synthesis of II-1

3.11 g (0.01 mol) V-2 were digested, together with 4.11 g (0.01 mol) P-6, in 60 ml formamide at 18–20° C. 5.6 ml (0.04 mol) triethylamine were added over 5 minutes (the starting materials were almost completely dissolved). After stirring for 20 hours at 20° C., 300 ml acetone were added (a dye was precipitated). After stirring for 2 hours at room temperature, the dye was filtered off under suction and thoroughly washed with acetone. The residue was dissolved in 40 ml formamide at 100° C., and was treated first with 2 ml triethylamine and then with 160 ml acetone. The batch was allowed to cool slowly to room temperature (RT), was stirred for a further 2 hours at RT, was filtered off under suction, and the residue was thoroughly washed with a 1:4 formamide:acetone mixture. This purification operation was repeated four times more, and the residue which then resulted was extracted by boiling for 2 hours with 200 ml acetone and was filtered off hot under suction. Yield: 2.4 g II-1 (34.2% theoretical).

Compound P-6 is a compound which is commonly used for the synthesis of spectral sensitisers, and can be obtained, for example, by the methods described in JP 9 146 209, JP 5 119 424 and JP 11 084 564.

Synthesis of II-42

2.34 g (7.5 mmol) V-2 were dissolved in 20 ml m-cresol at 85° C. with stirring, and the batch was treated with 2.25 ml (11.2 mmol) triethyl orthopropionate and was thereafter stirred for 30 minutes at 105° C. After cooling to 85° C., a further 2.34 g (7.5 mmol) V-2 were added, as a solution in 20 ml m-cresol, and the batch was treated with 2.6 ml triethylamine. After 90 minutes at 85° C., 80 ml acetone were added and the batch was stirred for a further 10 minutes under reflux, and was then allowed to cool to room temperature and stirred for a further 4 hours. The precipitated crude dye was filtered off under suction, thoroughly washed with acetone, dissolved in 10 ml formamide at 100° C. and filtered hot. 0.5 ml triethylamine and 40 ml acetone were added to the filtrate. After slow cooling of the batch to room temperature, the dye was filtered off under suction and the residue was extracted by boiling it in a mixture of 20 ml acetone and 1 ml triethylamine for 2 hours. After cooling to room temperature, the dye was filtered off under suction and thoroughly washed with acetone. The dye was subsequently dried under vacuum at 40° C. Yield: 3.49 g II-42 (61% theoretical).

Sensitiser II-55 can be obtained by the following synthesis route:

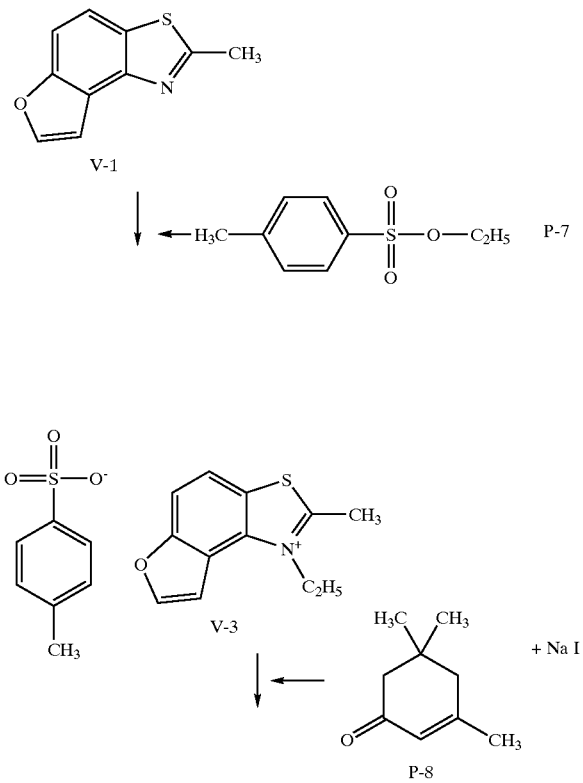

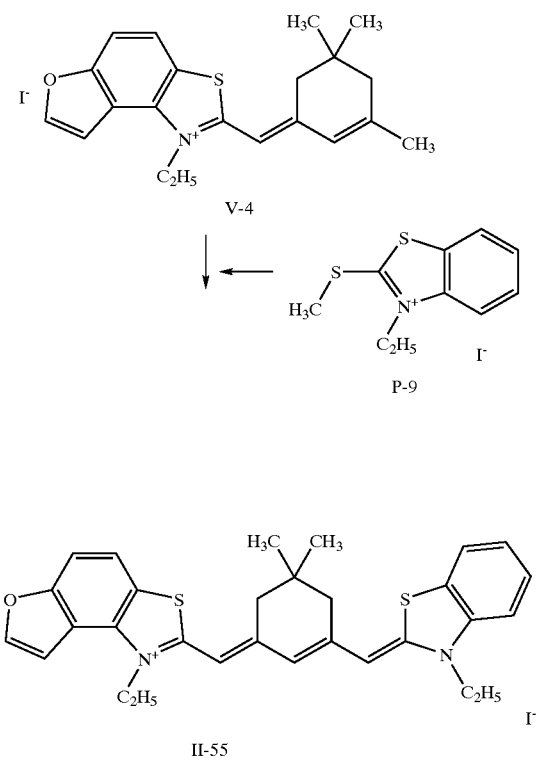

Synthesis of V-3

3.11 g (10 mmol) V-1 and 2.4 g (12 mmol) ethyl toluenesulphonate, P-7, were heated for 3 hours at 165° C. with stirring. After cooling to 80° C., 50 ml acetone were carefully added. The batch was allowed to cool slowly to room temperature, and was then cooled to 0° C. and was stirred for a further 2 hours at this temperature. After filtering under suction, the residue was extracted by boiling it with 40 ml acetone for 2 hours. Yield: 1.45 g V-3 (38% theoretical).

Synthesis of V-4

2,71 g (7 mmol) V-3 and 0.96 g (7 mmol) P-8 (obtainable from specialist chemical suppliers) were heated at 145° C. for 20 hours with stirring, under a nitrogen atmosphere. After cooling to room temperature, the residue was taken up in 10 ml ethanol and was treated with 5 ml of an ethanolic solution of NaI (1.5 g NaI). The batch was stirred for a further 2 hours, and was filtered off under suction and washed thoroughly with ethanol. The residue was dissolved in 20 ml of hot ethanol, filtered, and slowly cooled, with stirring, to room temperature. After stirring for a further 3 hours at room temperature, the precipitate was filtered off under suction and thoroughly washed with ethanol. The product was dried under vacuum at 40° C. Yield: 2.24 g V-4 (32% theoretical).

Synthesis of II-55

2.32 g (5 mmol) V-4 and 1.68 g (5 mmol) P-9 (e.g. the product obtainable according to U.S. Pat. No. 2,161,331 and Morgan, J. Chem. Soc. 1958, pages 854, 855 and 858) were digested together in 10 ml ethanol, were treated at room temperature, with stirring, with 0.95 g (9.4 mmol) triethylamine, and were subsequently heated under reflux for 30 minutes. After cooling to room temperature, the precipitated crude dye was filtered off under suction and was thoroughly washed with ethanol. The crude dye was dissolved in 8 ml m-cresol at 100° C. and was treated with 25 ml methanol. After cooling to room temperature, the batch was stirred for a further 1 hours at room temperature, and was filtered off under suction and thoroughly washed with methanol. This procedure was repeated twice more. The dye, which was still moist, was extracted by boiling it for 4 hours with 20 ml acetone, and after cooling to room temperature was filtered off under suction and washed with acetone, and was subsequently dried at 40° C. under vacuum. Yield: 0.63 g II-55 (25% theoretical).

Examples of modified synthesis routes:

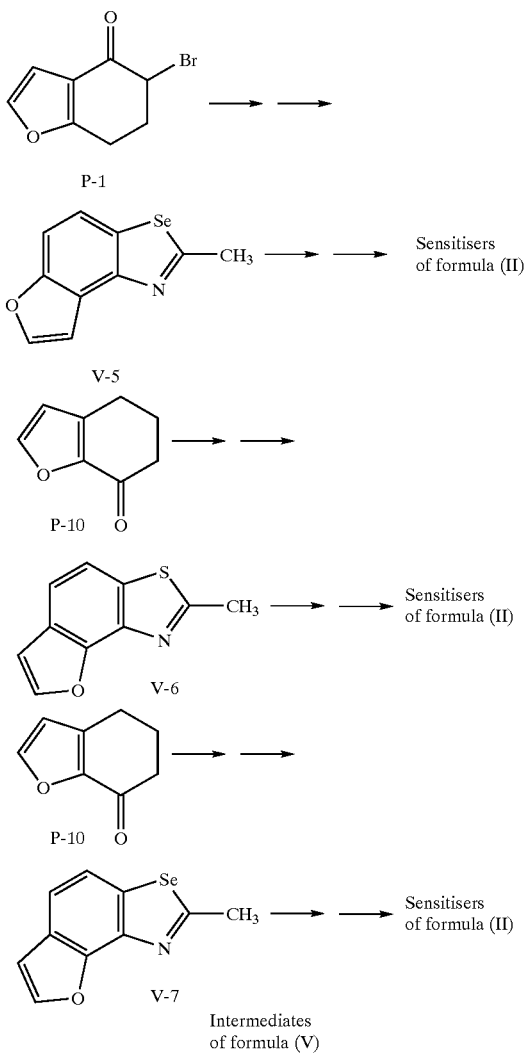

These syntheses can be carried out analogously to those described above. The preparation of compound P-10 is described in Tetrahedron Letters 27, 1127 (1986) and in Bull. Chem. Soc. Jpn. 71, 1437 (1998). The bromination of P-10 in the alpha-position to the carbonyl group, which is advantageous for further synthesis, can be effected analogously to the synthesis of P-1. The selenoacetamide which is required for the synthesis of selenazole bases, e.g. V-5 and V-7, can be obtained as described in J. Am. Chem. Soc. 57, 2494 (1935), for example.

Examples of colour photographic materials include colour negative films, colour reversal films, colour positive films, colour photographic paper, colour reversal photographic paper, and colour-sensitive materials for the colour diffusion transfer process or the silver halide bleaching process. A review is given in Research Disclosure 37038 (1995), and in Research Disclosure 38957 (1996).

Photographic materials consist of a support on which at least one light-sensitive silver halide emulsion layer is deposited. Thin films and foils are particularly suitable as supports. A review of support materials and of the auxiliary layers which are deposited on the front and back thereof is given in Research Disclosure 37254, Part 1 (1995), page 285 and in Research Disclosure 38957, Part XV (1996), page 627.

Colour photographic materials usually contain at least one red-sensitive, at least one green-sensitive and at least one blue-sensitive silver halide emulsion layer, and optionally contain intermediate layers and protective layers also.

Depending on the type of photographic material, these layers may be arranged differently. This will be illustrated for the most important products:

Colour photographic films such as colour negative films and colour reversal films comprise, in the following sequence on their support: 2 or 3 red-sensitive, cyan-coupling silver halide emulsion layers, 2 or 3 green-sensitive, magenta coupling silver halide emulsion layers, and 2 or 3 blue-sensitive, yellow-coupling silver halide emulsion layers. The layers of identical spectral sensitivity differ as regards their photographic speed, wherein the less sensitive partial layers are generally disposed nearer the support than are the more highly sensitive partial layers.

A yellow filter layer is usually provided between the green-sensitive and blue-sensitive layers, to prevent blue light from reaching the layers underneath.

The options for different layer arrangements and their effects on photographic properties are described in J. Inf. Rec. Mats., 1994, Vol. 22, pages 183–193, and in Research Disclosure 38957, Part XI (1996), page 624.

Colour photographic paper, which as a rule is less sensitive to light than is colour photographic film, usually comprises the following layers on the support, in the following sequence: a blue-sensitive, yellow-coupling silver halide emulsion layer, a green-sensitive, magenta coupling silver halide emulsion layer, and a red-sensitive, cyan-coupling silver halide emulsion layer. The yellow filter layer may be omitted.

Departures from the number and arrangement of the light-sensitive layers may be effected in order to achieve defined results. For example, all the high-sensitivity layers may be combined to form a layer stack and all the low-sensitivity layers may be combined to form another layer stack in a photographic film, in order to increase the sensitivity (DE-25 30 645).

The essential constituents of the photographic emulsion layer are binders, silver halide grains and colour couplers.

Information on suitable binders is given in Research Disclosure 37254, Part 2 (1995), page 286, and in Research Disclosure 38957, Part II.A (1996), page 598.

Information on suitable silver halide emulsions, their production, ripening, stabilisation and spectral sensitisation, including suitable spectral sensitisers, is given in Research Disclosure 37254, Part 3 (1995), page 286, in Research Disclosure 37038, Part XV (1995), page 89, and in Research Disclosure 38957, Part V.A (1996), page 603.

Photographic materials which exhibit camera-sensitivity usually contain silver bromide-iodide emulsions, which may also optionally contain small proportions of silver chloride. Photographic copier materials contain either silver chloride-bromide emulsions comprising up to 80 mole % AgBr, or silver chloride-bromide emulsions comprising more than 95 mole % AgCl.

Information on colour couplers is to be found in Research Disclosure 37254, Part 4 (1995), page 288, in Research Disclosure 37038, Part II (1995), page 80, and in Research Disclosure 38957, Part X.B (1996), page 616. The maximum absorption of the dyes formed from the couplers and from the colour developer oxidation product preferably falls within the following ranges: yellow couplers 430 to 460 nm, magenta couplers 540 to 560 nm, cyan couplers 630 to 700 nm.

In order to improve sensitivity, granularity, sharpness and colour separation, compounds are frequently used in colour photographic films which on reaction with the developer oxidation product release compounds which are photographically active, e.g. DIR couplers, which release a development inhibitor.

Information on compounds such as these, particularly couplers, is to be found in Research Disclosure 37254, Part 5 (1995), page 290, in Research Disclosure 37038, Part XIV (1995), page 86, and in Research Disclosure 38957, Part X.C (1996), page 618.

The colour couplers, which are mostly hydrophobic, and other hydrophobic constituents of the layers also, are usually dissolved or dispersed in high-boiling organic solvents. These solutions or dispersions are then emulsified in an aqueous binder solution (usually a gelatine solution), and after the layers have been dried are present as fine droplets (0.05 to 0.8 μm diameter) in the layers.

Suitable high-boiling organic solvents, methods of introduction into the layers of a photographic material, and other methods of introducing chemical compounds into photographic layers, are described in Research Disclosure 37254, Part 6 (1995), page 292.

The light-insensitive intermediate layers which are generally disposed between layers of different spectral sensitivity may contain media which prevent the unwanted diffusion of developer oxidation products from one light-sensitive layer into another light-sensitive layer which has a different spectral sensitivity.

Suitable compounds (white couplers, scavengers or DOP scavengers) are described in Research Disclosure 37254, Part 7 (1995), page 292, in Research Disclosure 37038, Part III (1995), page 84, and in Research Disclosure 38957, Part XD (1996), page 621 et seq.

The photographic material may additionally contain compounds which absorb UV light, brighteners, spacers, filter dyes, formalin scavengers, light stabilisers, anti-oxidants, $D_{Min}$ dyes, plasticisers (latices), biocides and additives for improving the dye-, and coupler stability, for reducing colour fogging and for reducing yellowing, and other substances. Suitable compounds are given in Research Disclosure 37254, Part 8 (1995), page 292, in Research Disclosure 37038, Parts IV, V, VI, VII, X, XI and XIII (1995), pages 84 et seq., and in Research Disclosure 38957, Parts VI, VIII, IX, X (1996), pages 607, 610 et seq.

The layers of colour photographic materials are usually hardened, i.e. the binder used, preferably gelatine, is crosslinked by suitable chemical methods.

Suitable hardener substances are described in Research Disclosure 37254, Part 9 (1995), page 294, in Research Disclosure 37038, Part XII (1995), page 86, and in Research Disclosure 38957, Part II.B (1996), page 599.

After image-by-image exposure, colour photographic materials are processed by different methods corresponding to their character. Details on the procedures used and the chemicals required therefor are published in Research Disclosure 37254, Part 10 (1995), page 294, in Research Disclosure 37038, Parts XVI to XXIII (1995), page 95 et seq., and in Research Disclosure 38957, Parts XVIII, XIX, XX (1996), page 630 et seq., together with examples of materials.

EXAMPLES

Example 1

| Production of emulsion | |
|---|---|
| solution 1 | 1100 g water |
|  | 140 g gelatine |
| solution 2 | 1860 g water |
|  | 360 g NaCl |
| solution 3 | 1800 g water |
|  | 1000 g AgNO$_3$ |

Solutions 2 and 3 were added to solution 1 simultaneously, at 50° C. over 300 minutes and at a pAg of 7.7 with intensive stirring. A silver chloride emulsion was obtained which had an average particle diameter of 0.85 μm. The ratio by weight of gelatine to AgNO$_3$ was 0.14. The emulsion was ultrafiltered, washed, and re-dispersed with an amount of gelatine such that the ratio by weight of gelatine to AgNO$_3$ was 0.56.

Ripening and Sensitisation

The emulsion was ripened at a pH of 5.3 with the optimum amount of gold(III) chloride and Na$_2$S$_2$O$_3$ at a temperature of 50° C. After chemical ripening, the emulsion was spectrally sensitised at 50° C. with 2.54 mmol/kg Ag of a dye as listed in Table 1, was stabilised with 0.5 g of compound ST-1/kg Ag and was subsequently treated with 0.6 mol % KBr (with respect to silver nitrate).

The individual layers, which were cast on to a polyethylene-coated paper support, contained the following amounts per m$^2$ of the substances listed below:

| AgCl corresponding to | 0.40 g AgNO$_3$ |
|---|---|
|  | 0.96 g gelatine |
|  | 0.55 g yellow coupler GB-1 |

-continued

| | |
|---|---|
| 0.21 g tricresyl phosphate | |
| 0.11 g dye stabiliser ST-2 | |

The material was hardened by depositing a protective layer comprising 0.92 g gelatine and 0.34 g of instant hardener (H-1) per m².

The sample which was thus produced was exposed for 40 msec behind a stepped photometric absorption wedge and was processed as follows, using Process AP 49:

| Colour developer-45 sec.-35° C. | |
|---|---|
| triethanolamine | 9.0 g |
| N,N-diethylhydroxylamine | 4.0 g |
| diethylene glycol | 0.05 g |
| 3-methyl-4-amino-N-ethyl-N-methane-sulphonamidoethyl-aniline sulphate | 5.0 g |
| potassium sulphite | 0.2 g |
| triethylene glycol | 0.05 g |
| potassium carbonate | 22 g |
| potassium hydroxide | 0.4 g |
| ethylenediaminetetraacetic acid, di-Na salt | 2.2 g |
| potassium chloride | 2.5 g |

-continued

| Colour developer-45 sec.-35° C. | |
|---|---|
| 1,2-dihydroxybenzene-3,4,6-trisulphonic acid, trisodium salt | 0.3 g |
| made up with water to 1000 ml (pH 10.0) | |

| Bleach hardener-45 sec.-35° C. | |
|---|---|
| ammonium thiosulphate | 75 g |
| sodium hydrogen sulphite | 13.5 g |
| ammonium acetate | 2.0 g |
| ethylenediaminetetraacetic acid (iron ammonium salt) | 57 g |
| 25% ammonia | 9.5 g |
| made up with vinegar to 1000 ml (pH 5.5) | |

Washing—2 min—33° C.

Drying

The blue-sensitivities and $D_{min}$ values which were determined for the materials produced in this manner are listed in Table 1 as relative values, wherein the sensitivity/speed of sample 2 and the $D_{min}$ value of sample 7 were arbitrarily set to 1.00.

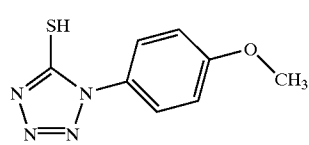

ST-1

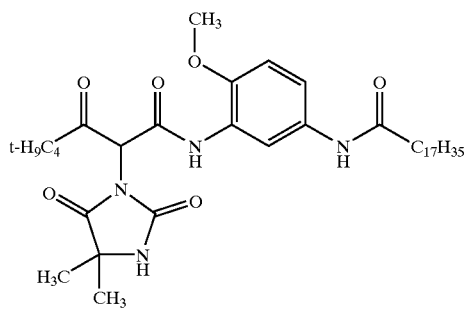

GB-1

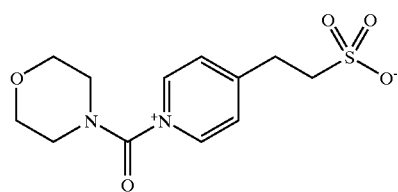

H-1

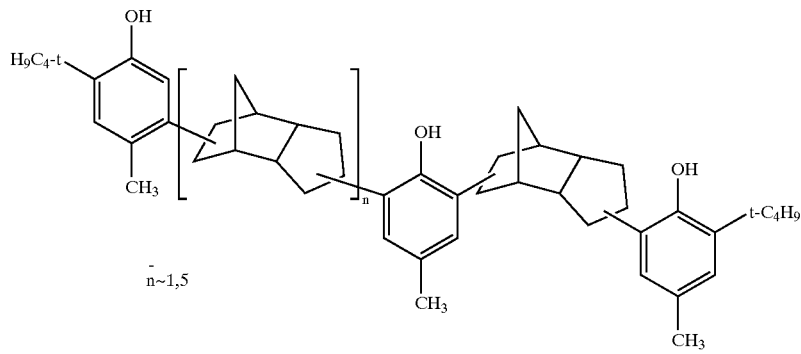

ST-2

TABLE 1

| Sample | Dye | Rel. speed | Rel. D$_{min}$ | |
|---|---|---|---|---|
| 1.1 | II-1 | 0.98 | 0.82 | invention |
| 1.2 | II-7 | 1.00 | 0.79 | invention |
| 1.3 | II-4 | 0.96 | 0.85 | invention |
| 1.4 | II-5 | 0.99 | 0.85 | invention |
| 1.5 | VI-21 | 0.89 | 0.94 | comparison |
| 1.6 | VI-22 | 0.90 | 0.99 | comparison |
| 1.7 | VI-23 | 0.92 | 1.00 | comparison |

It can clearly be seen from Table 1 that the speed/fogging ratio is considerably improved by the sensitisers according to the invention. Moreover, the very much lower sensitiser staining of the samples according to the invention could be seen by visual comparison.

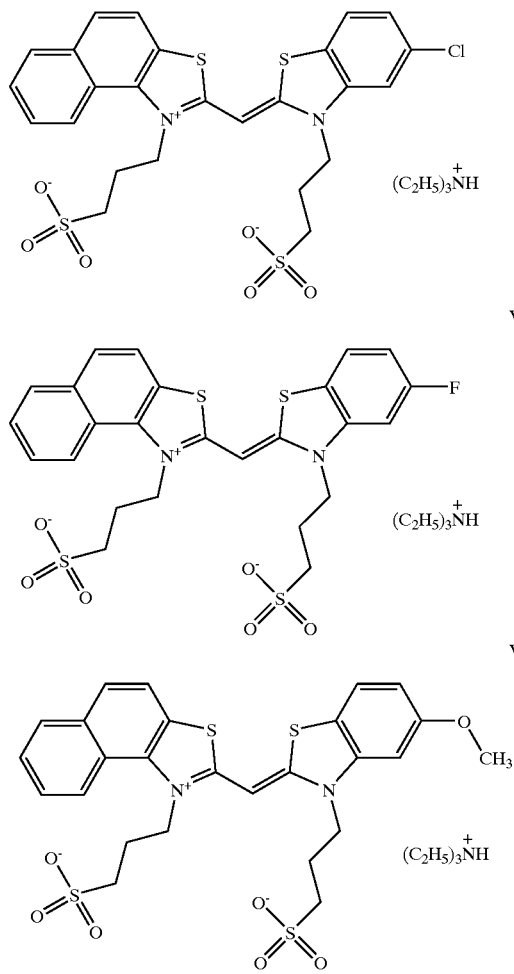

Example 2
Production of Emulsions and Sensitisation

The following solutions were each made up with demineralised water:

| solution 1 | 4000 g | water |
|---|---|---|
| | 500 g | gelatine |
| solution 2 | 6700 g | water |
| | 1300 g | NaCl |
| | 0.4 mg | K$_2$IrCl$_6$ |
| | 0.2 mg | Na$_3$RhCl$_6$ |
| solution 3 | 6500 g | water |
| | 3600 g | AgNO$_3$ |

Solutions 2 and 3 were added simultaneously to solution 1 at 45° C. over 70 minutes at a pAg of 7.7 and with intensive stirring. A silver chloride emulsion was obtained which had an average particle diameter of 0.5 μm. The ratio by weight of gelatine to AgNO$_3$ was 0.14. The emulsion was ultrafiltered and washed in the known manner, and was re-dispersed with an amount of gelatine such that ratio by weight of gelatine to AgNO$_3$ was 0.56. The silver halide content was 1.5 mol per kg emulsion. The emulsion was treated, with stirring, with 18 μmol gold(III) chloride/mol AgNO$_3$ and with 7 μmol Na$_2$S$_2$O$_3$/mol AgNO$_3$ at a pH of 5.3. After 5 minutes, 200 mg of compound ST-1 were added and the batch was subsequently ripened for 3 hours at 70° C. with stirring. After cooling to 50° C., the product was spectrally sensitised by adding 50 μmol of spectral sensitiser per mol AgNO$_3$ (dissolved in methanol, 0.1% by weight solution) as listed in Table 2, and was stabilised by 2 g ST-3/kg AgNO$_3$.

A colour photographic recording material was produced, which comprised the following layers on a polyethylene-coated paper support:

| 1.) | photographic layer (red-sensitive, cyan-coupling) | |
|---|---|---|
| | emulsion as AgNO$_3$ | 0.30 g/m$^2$ |
| | cyan coupler BG-1 | 0.42 g/m$^2$ |
| | tricresyl phosphate | 0.42 g/m$^2$ |
| 2.) | protective layer | |
| | gelatine | 1.60 g/m$^2$ |
| 3.) | hardener layer | |
| | hardener H-1 | 0.20 g/m$^2$ |

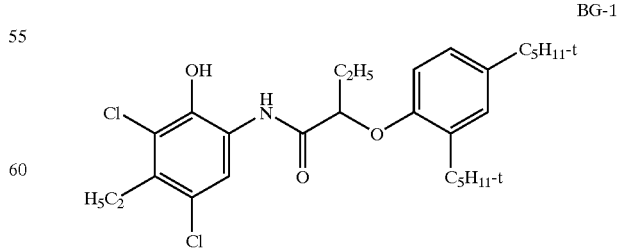

The material was exposed for 40 msec through a stepped photometric absorption wedge and was processed using Process AP 94.

The red-sensitivities and $D_{min}$ values were determined for the materials produced in this manner. The relative values are listed in Table 2, wherein the sensitivity/speed of sample 2.2 and the $D_{min}$ value of sample 2.6 were arbitrarily set to 1.00.

TABLE 2

| Sample | Dye | Rel. Speed | Rel. $D_{min}$ | |
|---|---|---|---|---|
| 2.1 | II-54 | 0.97 | 0.84 | invention |
| 2.2 | II-55 | 1.00 | 0.82 | invention |
| 2.3 | II-60 | 0.99 | 0.80 | invention |
| 2.4 | X-1 | 0.78 | 0.97 | comparison |
| 2.5 | X-2 | 0.89 | 0.97 | comparison |
| 2.6 | X-3 | 0.86 | 1.00 | comparison |
| 2.7 | X-4 | 0.86 | 0.99 | comparison |

It can clearly be seen from Table 2 that the speed/fogging ratio is considerably improved by the sensitisers according to the invention. Moreover, the very much lower sensitiser staining of the samples according to the invention could be seen by visual comparison.

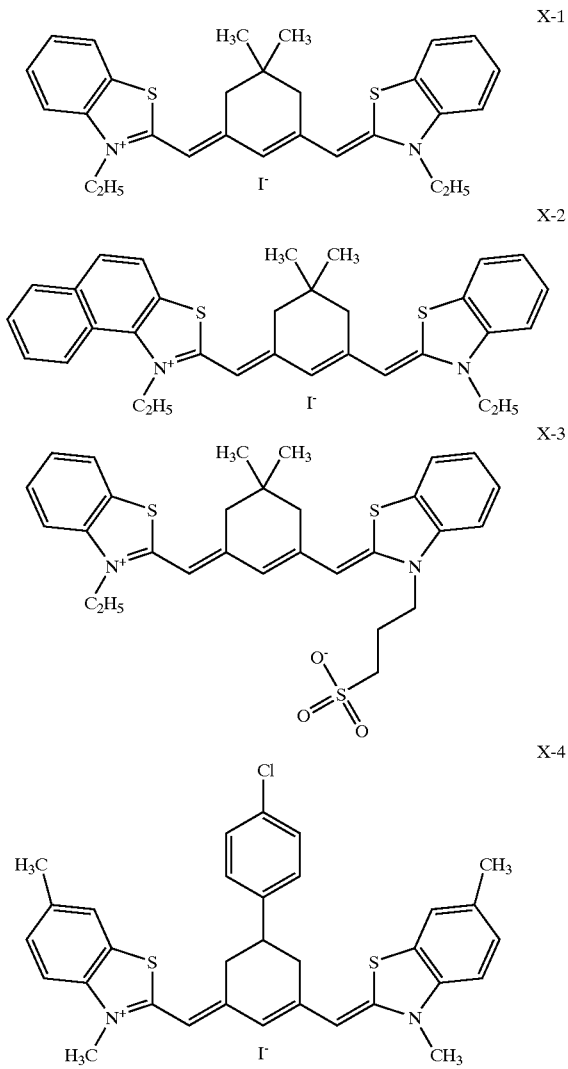

Example 3

Crude Emulsion

A solution of 144 g of inert gelatine and 107 g potassium bromide in 18 kg water was placed in a vessel and stirred. An aqueous solution of silver nitrate (47 g silver nitrate in 550 g water) and an aqueous halide solution (33 g potassium bromide in 550 g water) were added as a double inflow over 30 seconds. This was followed by the addition of 395 g of inert gelatine in 4 kg water. After heating to 74° C., an aqueous solution of silver nitrate (114 g silver nitrate in 1.4 kg water) was added over 20 minutes.

Thereafter, the second double inflow was also effected at 74° C. This comprised the addition of an aqueous solution of silver nitrate (1339 g silver nitrate in 8.3 kg water) and of an aqueous halide solution (1117 g potassium bromide in 9.8 kg water), over 50 minutes with an increasing rate of addition. The rate of addition here was increased in 10 steps from an initial value of 70 ml/minute to a rate of 400 ml/minute. During the inflow, the pBr of the dispersion medium was held constant at 2.3.

After the last inflow, the emulsion was cooled to 25° C., was flocculated at pH 3.5 by adding polystyrenesulphonic acid, and was subsequently washed at 20° C. Thereafter, the flocculate was made up with water to 7.5 kg and was re-dispersed at pH 6.5 and at a temperature of 50° C.

The emulsion had a content of more than 80% (with respect to the projected area of the crystals) of hexagonal platelets with an aspect ratio (average diameter of the circle equivalent to the projected area/thickness of the platelets) of 8, and had an adjacent edge ratio ranging from 1:1 to 1.5:1. The grain size was 0.55 μm and the distribution width was 18%.

The silver halide emulsion was chemically ripened at 55° C., pAg 7.4 and pH 6.5 with 5.0 μmol tetrachloroauric acid, 690 μm potassium thiocyanate and 20 μmol sodium thiosulphate per mol $AgNO_3$.

The emulsion was spectrally sensitised. The procedure employed here was to add 350 μmol 4-hydroxy-6-methyl-1,3,3a, 7-tetraazaindene per 100 g $AgNO_3$ to the emulsion, which had been heated to 40° C., followed by the addition of 500 μmol of spectral sensitiser as listed in Table 3, per mol $AgNO_3$, wherein the sensitiser was dissolved in methanol or in a mixture of methanol and phenoxyethanol. Thereafter, the emulsion was stirred for a further 20 minutes at 40° C.

The emulsion was treated with an emulsion of cyan coupler BG-2 and with an emulsion of cyan coupler BG-3 and was deposited on a film base of thickness 120 μm comprising cellulose acetate on a substrate.

The cast individual layers contained the following amounts of substances per $m^2$:

| | |
|---|---|
| AgBr corresponding to | 0.63 g $AgNO_3$ |
| | 1.38 g gelatine |
| | 0.25 g cyan coupler BG-2 |
| | 0.37 g cyan coupler BG-3 |
| | 0.62 g tricresyl phosphate. |

The material was hardened by depositing a protective layer comprising 0.2 g gelatine and 0.3 g of an instant hardener (H-1) per $m^2$.

The speeds of the materials produced in this manner were determined. For this purpose, the materials were exposed behind a graduated wedge filter and were subjected to colour negative processing according to "The Journal of Photographic Science 1974, pages 597, 598". The results are listed in Table 3 as relative values, wherein the sensitivity/speed of sample 3.3 and the $D_{min}$ value of sample 3.10 were arbitrarily set to 1.00.

BG-2

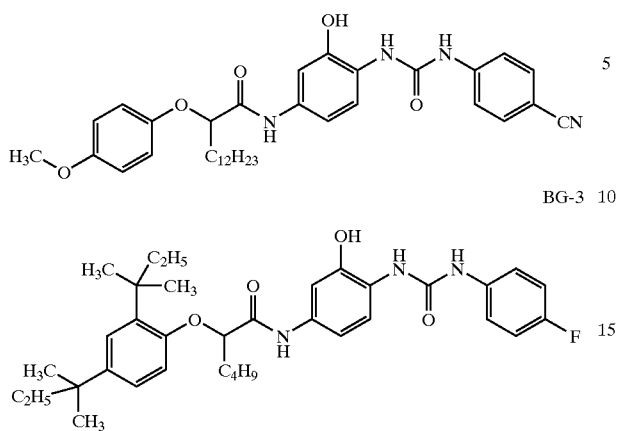

BG-3

TABLE 3

| Sample | Dye | Rel. Speed | Rel. $D_{min}$ | |
|---|---|---|---|---|
| 3.1 | II-25 | 0.96 | 0.70 | invention |
| 3.2 | II-26 | 0.97 | 0.70 | invention |
| 3.3 | II-27 | 1.00 | 0.61 | invention |
| 3.4 | II-33 | 0.94 | 0.65 | invention |
| 3.5 | VI-24 | 0.88 | 0.81 | comparison |
| 3.6 | VI-25 | 0.84 | 0.79 | comparison |
| 3.7 | VI-26 | 0.90 | 0.79 | comparison |
| 3.8 | VI-27 | 0.74 | 0.86 | comparison |
| 3.9 | II-43 | 0.94 | 0.88 | invention |
| 3.10 | VI-28 | 0.76 | 1.00 | comparison |

It can clearly be seen from Table 3 that the speed/fogging ratio is considerably improved by the sensitisers according to the invention. Moreover, the very much lower sensitiser staining of the samples according to the invention could be seen by visual comparison.

VI-24

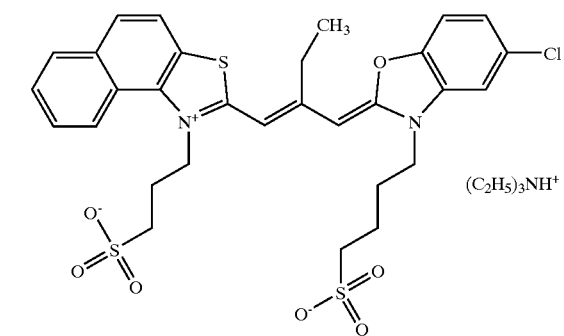

VI-25

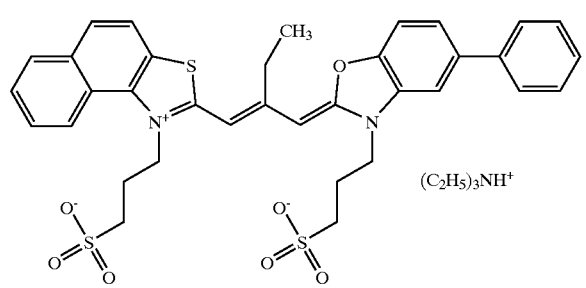

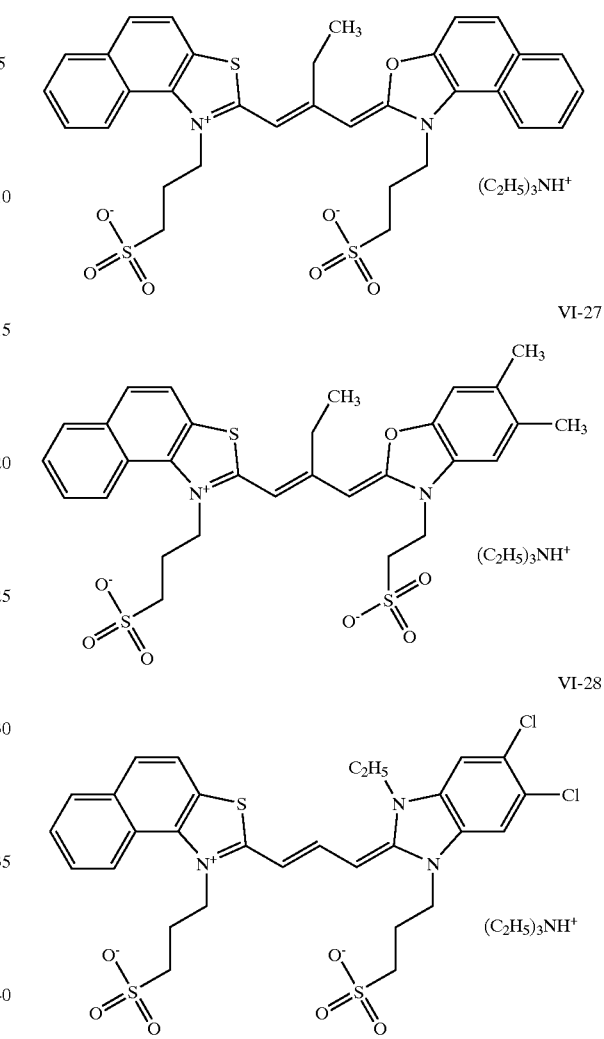

Example 4

The preparation of the crude photographic emulsion, and the ripening and spectral sensitisation thereof, were effected analogously to Example 1, except that instead of one sensitiser a mixture of sensitisers was used in each case (the sum of the sensitisers in a mixture was always normalised to 500 μmol/100 g AgNO$_3$). The sensitisers used and the results obtained therewith are given as relative values in Tables 4 and 5, wherein the speeds of the samples 4.2 and 5.2 and the $D_{min}$ value of samples 4.6 and 5.6 were arbitrarily set to 1.00.

TABLE 4

| Sample | Dyes | Mixture ratio | Rel. Speed | Rel. $D_{min}$ | |
|---|---|---|---|---|---|
| 4.1 | II-25/VI-13 | 2/1 | 0.98 | 0.81 | invention |
| 4.2 | II-26/VI-13 | 2/1 | 1.00 | 0.83 | invention |
| 4.3 | II-33/VI-15 | 2/1 | 0.98 | 0.81 | invention |
| 4.4 | VI-24/VI-13 | 2/1 | 0.91 | 0.99 | comparison |
| 4.5 | VI-25/VI-13 | 2/1 | 0.93 | 0.99 | comparison |
| 4.6 | VI-25/VI-15 | 2/1 | 0.90 | 1.00 | comparison |

TABLE 5

| Sample | Dyes | Mixture ratio | Rel. Speed | Rel. $D_{min}$ | |
|---|---|---|---|---|---|
| 5.1 | II-25/VI-13/II-42 | 1/2/0.1 | 0.97 | 0.90 | invention |
| 5.2 | II-26/VI-13/II-42 | 1/2/0.1 | 1.00 | 0.89 | invention |
| 5.3 | II-33/VI-15/II-42 | 1/2/0.1 | 0.97 | 0.90 | invention |
| 5.4 | VI-24/VI-13/VI-14 | 1/2/0.1 | 0.91 | 0.94 | comparison |
| 5.5 | VI-25/VI-13/VI-14 | 1/2/0.1 | 0.90 | 0.95 | comparison |
| 5.6 | VI-27/VI-15/VI-14 | 1/2/0.1 | 0.88 | 1.00 | comparison |

It can clearly be seen from Tables 4 and 5 that the speed/fogging ratio is considerably improved by the sensitisers according to the invention, wherein the absolute speed could be increased by the admixture. Moreover, it could be seen from a visual comparison that there the samples according to the invention exhibited much less sensitiser staining, despite the admixture thereof with a sensitiser of formula (VI).

What is claimed is:

1. A photographic material comprising a support and at least one light-sensitive silver halide emulsion layer which contains the compound of formula (II)

(II)

wherein $X^1$ is $C(R^5, R^6)$, $NR^7$, O, S or Se, $X^2$ is O, S, Se or $NR^{13}$, $R^3$ with $R^4$, jointly are the remaining members for the completion of a substituted or unsubstituted condensed furano ring system, and the $R^2$ radical, is H, a halogen, SH, CN, $CF_3$, alkyl, aryl, heterocyclyl, alkoxy, aryloxy, alkylthio or arylthio, $R^{10}$ to $R^{12}$, independently of each other, are H, a halogen, SH, CN, $CF_3$, alkyl, aryl, heterocyclyl, alkoxy, aryloxy, alkylthio or arylthio, or $R^{10}$ with $R^{11}$, or $R^{11}$ with $R^{12}$, each jointly are the remaining members for the completion of a substituted or unsubstituted condensed furano, benzene or naphthalene ring system and the $R^{10}$ or $R^{12}$ radical, which is not part of the ring system, denotes H, a halogen, SH, CN, $CF_3$, alkyl, aryl, heterocyclyl, alkoxy, aryloxy, alkylthio or arylthio, $R^5$ to $R^7$ independently of each other are alkyl, alkylene-$SO_3Z^1$ or alkylene-$CO_2Z^1$, wherein the alkyl and alkylene can be further substituted and each comprise 1 to 6 C atoms, $R^8$ and $R^9$ independently of each other are alkyl, alkylene-$SO_3Z^1$, alkylene-$CO_2Z^1$ or alkylene-$Y^2$—$N(Z^1)$—$Y^3$-alkyl, wherein the alkyl and alkylene are optionally substituted and each comprise 1 to 6 C atoms, $R^{13}$ is alkyl, alkylene-$SO_3Z^1$ or alkylene-$CO_2Z^1$, wherein the alkyl and alkylene are optionally substituted and each comprise 1 to 6 C atoms, $Z^1$ is H or a negative charge, $Y^2$ and $Y^3$, independently of each other, are —$S(=O)_2$— or —$C(=O)$—, and $M^1$ is a counterion which may be necessary for charge equalization, $L^1$, $L^2$ and $L^3$ independently of each other are a substituted or unsubstituted methine group, which can be a constituent of one or more carbocyclic rings, and n is 0, 1, 2 or 3.

2. The photographic material according to claim 1 wherein $X^1$ is S or Se, and $R^{10}$ to $R^{12}$, independently of each other, are H, a halogen, CN, $CF_3$, alkyl, aryl, heterocyclyl, alkoxy, aryloxy, alkylthio or arylthio, or $R^{10}$ with $R^{11}$, or $R^{11}$ with $R^{12}$, each jointly are the remaining members for the completion of a substituted or unsubstituted condensed benzene or naphthalene ring system.

3. The photographic material according to claim 1, wherein n denotes 0, 1 or 2.

4. The photographic material according to claim 1, wherein the compound of the formula (II) is a compound of formulae (III) or (IV)

(III)

wherein (IV)

$R^{14}$ and $R^{15}$, independently of each other, are H, a halogen, CN, $CF_3$, alkyl, aryl, heterocyclyl, alkoxy, aryloxy, alkylthio or arylthio.

5. The photographic material according to claim 1, wherein the silver halide emulsion layer further contains at least one dye of formula (VI) wherein (VI)

$X^3$ and $X^4$, independently of each other, are O, S, Se or $NR^{24}$, $R^{16}$ to $R^{21}$, independently of each other, are H, a halogen, CN, $CF_3$, alkyl, aryl, heterocyclyl, alkoxy, aryloxy, alkylthio or arylthio, $R^{22}$ and $R^{23}$, independently of each other, are alkyl, alkylene-$SO_3Z^2$, alkylene-$CO_2Z^2$ or alkylene-$Y^4$—N ($Z^2$)—$Y^5$-alkyl, wherein the alkyl and alkylene are optionally substituted and each comprise 1 to 6 C atoms, $R^{24}$ is alkyl, alkylene-$SO_3Z^2$ or alkylene-$CO_2Z^2$, wherein the alkyl and alkylene are optionally substituted and each comprise 1 to 6 C atoms, $Z^2$ is H or a negative charge, $L^4$, $L^5$ and $L^6$ independently of each other are a substituted or unsubstituted methine group, which can be a constituent of one or more carbocyclic rings, m is 0 or 1, $Y^4$ and $Y^5$, independently of each other, are —S(=O)$_2$— or —C(=O)—, and $M^2$ is a counterion which may be necessary for charge equalization, wherein either $R^{16}$ with $R^{17}$, or $R^{17}$ with $R^{18}$, and/or either $R^{19}$ with $R^{20}$, or $R^{20}$ with $R^{21}$ can each jointly denote the remaining members for the completion of a substituted or unsubstituted condensed benzene or naphthalene ring system.

6. The photographic material according to claim 1, wherein at least 95 mol percent of the silver halide crystals of the light-sensitive layer contain silver chloride, and contain not more than 1 mol percent silver iodide.

7. The photographic material according to claim 1, wherein n is equal to 0 and the silver halide emulsion layer contains at least one yellow coupler.

8. The photographic material according to claim 1, wherein the silver halide emulsion layer contains tabular crystals with an aspect ratio of at least 3:1.

9. The photographic material according to claim 8, wherein the aspect ratio is greater than 6:1.

10. The photographic material according to claim 8, wherein the aspect ratio is greater than 10:1.

11. The photographic material according to claim 1, wherein silver halide emulsion layer has a bromide content of at least 80 mol %, a maximum chloride content of 15 mol % and a maximum iodide content of 12 mol %.

12. The photographic material according to claim 1, wherein $R^3$ with $R^4$, jointly are the remaining members for the completion of a substituted or unsubstituted condensed furano ring system, and the $R^2$ radical, is H, a halogen, SH, CN, $CF_3$, alkyl, phenyl, heterocyclyl, alkoxy, aryloxy, alkylthio or arylthio, $R^{10}$ to $R^{12}$, independently of each other, are H, a halogen, SH, CN, $CF_3$, alkyl, phenyl, heterocyclyl, alkoxy, aryloxy, alkylthio or arylthio, or $R^{10}$ with $R^{11}$, or $R^{11}$ with $R^{12}$, each jointly are the remaining members for the completion of a substituted or unsubstituted condensed furano, benzene or naphthalene ring system and the $R^{10}$ or $R^{12}$ radical, which is not part of the ring system, denotes H, a halogen, SH, CN, $CF_3$, alkyl, phenyl, heterocyclyl, alkoxy, aryloxy, alkylthio or arylthio.

13. The photographic material according to claim 2, wherein $R^{10}$ to $R^{12}$, independently of each other, are H, a halogen, CN, $CF_3$, alkyl, phenyl, heterocyclyl, alkoxy, aryloxy, alkylthio or arylthio, or $R^{10}$ with $R^{11}$, or $R^{11}$ with $R^{12}$, each jointly are the remaining members for the completion of a substituted or unsubstituted condensed benzene or naphthalene ring system.

14. The photographic material according to claim 4, wherein $R^{14}$ and $R^{15}$, independently of each other, are H, a halogen, CN, $CF_3$, alkyl, phenyl, heterocyclyl, alkoxy, aryloxy, alkylthio or arylthio.

15. The photographic material according to claim 5, wherein $R^{16}$ to $R^{21}$, independently of each other, are H, a halogen, CN, $CF_3$, alkyl, phenyl, heterocyclyl, alkoxy, aryloxy, alkylthio or arylthio.

* * * * *